(12) United States Patent
Hawes et al.

(10) Patent No.: US 12,193,511 B2
(45) Date of Patent: **\*Jan. 14, 2025**

(54) E-VAPING DEVICE

(71) Applicant: Altria Client Services LLC, Richmond, VA (US)

(72) Inventors: Eric Hawes, Midlothian, VA (US); Raymond W. Lau, Glen Allen, VA (US); Mik Dahl, Lapu-Lapu (PH); Jon Jarantilla, Lapu-Lapu (PH); Galen Salvador, Lapu-Lapu (PH); Jose Jesus Paolo Montalvan, Mandaue (PH); Jeroen Kok, Amsterdam (NL)

(73) Assignee: Altria Client Services LLC, Richmond, VA (US)

( * ) Notice: Subject to any disclaimer, the term of this patent is extended or adjusted under 35 U.S.C. 154(b) by 310 days.

This patent is subject to a terminal disclaimer.

(21) Appl. No.: 17/895,422

(22) Filed: Aug. 25, 2022

(65) Prior Publication Data

US 2022/0400763 A1    Dec. 22, 2022

Related U.S. Application Data

(63) Continuation of application No. 16/196,344, filed on Nov. 20, 2018, now Pat. No. 11,445,759.

(51) Int. Cl.
*A24F 40/485* (2020.01)

(52) U.S. Cl.
CPC .................. *A24F 40/485* (2020.01)

(58) Field of Classification Search
CPC ......... A24F 40/10; A24F 15/015; A24F 40/40
See application file for complete search history.

(56) References Cited

U.S. PATENT DOCUMENTS

| 9,247,773 B2 | 2/2016 | Memari et al. |
| 9,254,007 B2 | 2/2016 | Liu |
| 9,308,336 B2 | 4/2016 | Newton |

(Continued)

FOREIGN PATENT DOCUMENTS

| CN | 203538369 U | 4/2014 |
| CN | 203748684 U | 8/2014 |

(Continued)

OTHER PUBLICATIONS

Anonymous: "iJust 2 Airflow Control Ring." Retrieved from the Internet on Nov. 16, 2018. URL: https://www.eleafus.com/ijust-2-airflow-control-ring.html.

(Continued)

*Primary Examiner* — Michael H. Wilson
*Assistant Examiner* — Stephanie Lynn Moore
(74) *Attorney, Agent, or Firm* — Harness, Dickey & Pierce, P.L.C.

(57) ABSTRACT

Some example embodiments include a reservoir assembly for an e-vaping device that may include a reservoir, a first bayonet connector assembly, and a conduit extending from a vaporizer assembly and into a space defined by the first bayonet connector assembly. The first bayonet connector assembly may detachably couple with a second bayonet connector assembly of an outlet assembly to establish a bayonet interface connection between the reservoir and the outlet assembly, such that the conduit is in fluid communication with the exterior of the reservoir assembly through an interior of the outlet assembly.

20 Claims, 14 Drawing Sheets

(56) References Cited

U.S. PATENT DOCUMENTS

| | | |
|---|---|---|
| 9,750,282 B2 | 9/2017 | Liu |
| 9,795,169 B1 | 10/2017 | Zhu |
| 9,814,264 B2 | 11/2017 | Coelho Belo Fernandes De Carvalho |
| 9,907,341 B1 | 3/2018 | Zhu |
| 9,961,942 B2 | 5/2018 | Liu |
| 9,993,025 B2 | 6/2018 | Alarcon et al. |
| 11,071,326 B2 | 7/2021 | Hawes et al. |
| 2014/0109921 A1 | 4/2014 | Chen |
| 2014/0290674 A1 | 10/2014 | Liu |
| 2015/0128971 A1 | 5/2015 | Verleur et al. |
| 2015/0196055 A1 | 7/2015 | Liu |
| 2015/0335071 A1 | 11/2015 | Brinkley et al. |
| 2016/0007654 A1 | 1/2016 | Zhu |
| 2016/0073692 A1 | 3/2016 | Alarcon et al. |
| 2016/0095357 A1 | 4/2016 | Burton |
| 2016/0120226 A1 | 5/2016 | Rado |
| 2016/0120227 A1 | 5/2016 | Levitz et al. |
| 2016/0157522 A1 | 6/2016 | Zhu |
| 2016/0219938 A1 | 8/2016 | Mamoun et al. |
| 2016/0262452 A1 | 9/2016 | Zhu |
| 2016/0286860 A1 | 10/2016 | Flayler |
| 2017/0001854 A1 | 1/2017 | Li et al. |
| 2017/0013880 A1 | 1/2017 | O'Brien et al. |
| 2017/0027227 A1 | 2/2017 | Lipowicz |
| 2017/0065001 A1 | 3/2017 | Li et al. |
| 2017/0071251 A1 | 3/2017 | Goch |
| 2017/0105451 A1 | 4/2017 | Fornarelli |
| 2017/0113007 A1 | 4/2017 | Wu |
| 2017/0156408 A1 | 6/2017 | Li et al. |
| 2017/0188636 A1 | 7/2017 | Li et al. |
| 2017/0208869 A1 | 7/2017 | Li et al. |
| 2017/0238614 A1 | 8/2017 | Li et al. |
| 2017/0258132 A1 | 9/2017 | Rostami et al. |
| 2017/0280778 A1 | 10/2017 | Force |
| 2017/0290370 A1 | 10/2017 | Garthaffner et al. |
| 2017/0325503 A1 | 11/2017 | Liu |
| 2017/0347705 A1 | 12/2017 | Li |
| 2017/0354180 A1 | 12/2017 | Fornarelli |
| 2018/0007961 A1 | 1/2018 | Zhu |
| 2018/0007966 A1 | 1/2018 | Li et al. |
| 2018/0018471 A1 | 1/2018 | Kim et al. |
| 2018/0020726 A1 | 1/2018 | Alarcon et al. |
| 2018/0035718 A1 | 2/2018 | Liu |
| 2018/0077967 A1 | 3/2018 | Hatton et al. |
| 2018/0077968 A1 | 3/2018 | Qiu |
| 2018/0098573 A1 | 4/2018 | Yu et al. |
| 2018/0098575 A1 | 4/2018 | Liu |
| 2018/0110940 A1 | 4/2018 | Suzuki et al. |
| 2018/0168236 A1 | 6/2018 | Qiu |
| 2018/0184710 A1 | 7/2018 | Tucker et al. |
| 2018/0199631 A1 | 7/2018 | Chen et al. |
| 2018/0256834 A1 | 9/2018 | Hepworth et al. |
| 2018/0263294 A1 | 9/2018 | Qiu |
| 2018/0279691 A1 | 10/2018 | Li et al. |
| 2018/0280636 A1 | 10/2018 | Jiang et al. |

FOREIGN PATENT DOCUMENTS

| | | | |
|---|---|---|---|
| CN | 104082863 A | 10/2014 | |
| CN | 203851819 U | 10/2014 | |
| CN | 203860454 U | 10/2014 | |
| CN | 203860455 U | 10/2014 | |
| CN | 104207330 A | 12/2014 | |
| CN | 203986123 U | 12/2014 | |
| CN | 204048044 U | 12/2014 | |
| CN | 204104840 U | 1/2015 | |
| CN | 104544568 A | 4/2015 | |
| CN | 204861175 U | 12/2015 | |
| CN | 204994614 U | 1/2016 | |
| CN | 105310112 A | 2/2016 | |
| CN | 205082671 U | 3/2016 | |
| CN | 105722417 A | 6/2016 | |
| CN | 105768236 A | 7/2016 | |
| CN | 205390305 U | 7/2016 | |
| CN | 105815810 A | 8/2016 | |
| CN | 105942581 A | 9/2016 | |
| CN | 205695706 U | 11/2016 | |
| CN | 106231937 A | 12/2016 | |
| CN | 205865989 U | 1/2017 | |
| CN | 106418714 A | 2/2017 | |
| CN | 106666833 A | 5/2017 | |
| CN | 107095346 A | 8/2017 | |
| CN | 206380711 U | 8/2017 | |
| CN | 206413751 U | 8/2017 | |
| CN | 206453250 U | 9/2017 | |
| CN | 206534130 U | 10/2017 | |
| CN | 107373758 A | 11/2017 | |
| CN | 107411173 A | 12/2017 | |
| CN | 107411176 A | 12/2017 | |
| CN | 206808661 U | 12/2017 | |
| CN | 206866629 U | 1/2018 | |
| CN | 206978739 U | 2/2018 | |
| CN | 206978745 U | 2/2018 | |
| CN | 207040881 U | 2/2018 | |
| CN | 207100510 U | 3/2018 | |
| CN | 207167762 U | 4/2018 | |
| CN | 207185918 U | 4/2018 | |
| CN | 207252783 U | 4/2018 | |
| CN | 107981418 A | 5/2018 | |
| CN | 207306063 U | 5/2018 | |
| CN | 207306075 U | 5/2018 | |
| CN | 207306079 U | 5/2018 | |
| CN | 108135290 A | 6/2018 | |
| CN | 108348709 A | 7/2018 | |
| DE | 202014001717 U1 | 5/2015 | |
| DE | 102015102894 A1 | 8/2015 | |
| EP | 2856892 A1 | 4/2015 | |
| EP | 3031339 A1 | 6/2016 | |
| EP | 3254571 A1 | 12/2017 | |
| EP | 3275322 A1 | 1/2018 | |
| EP | 3305110 A2 | 4/2018 | |
| EP | 3338571 A2 | 6/2018 | |
| JP | 2014-138863 A | 7/2014 | |
| JP | 2015-519903 A | 7/2015 | |
| JP | 2017-517279 A | 6/2017 | |
| JP | 3214915 U | 2/2018 | |
| JP | 2018-527901 A | 9/2018 | |
| JP | 2018-527907 A | 9/2018 | |
| KR | 10-2015-0016307 A | 2/2015 | |
| KR | 2016-0086749 A | 7/2016 | |
| KR | 2018-0034344 A | 4/2018 | |
| KR | 2018-0123683 A | 11/2018 | |
| RU | 2608689 C1 | 1/2017 | |
| RU | 2614600 C2 | 3/2017 | |
| RU | 2623922 C2 | 6/2017 | |
| RU | 2665451 C1 | 8/2018 | |
| WO | WO-2014/187770 A2 | 11/2014 | |
| WO | WO-2014201432 A1 | 12/2014 | |
| WO | WO-2015/062136 A1 | 5/2015 | |
| WO | WO-2015/117704 A1 | 8/2015 | |
| WO | WO-2016/008217 A1 | 1/2016 | |
| WO | WO-2016/045058 A1 | 3/2016 | |
| WO | WO-2016/096745 A1 | 6/2016 | |
| WO | WO-2016/096780 A1 | 6/2016 | |
| WO | WO-2016090426 A1 | 6/2016 | |
| WO | WO-2016119098 A1 | 8/2016 | |
| WO | WO-2016/145612 A1 | 9/2016 | |
| WO | WO-2016141508 A1 | 9/2016 | |
| WO | WO-2016145613 A1 | 9/2016 | |
| WO | WO-2016/154994 A1 | 10/2016 | |
| WO | WO-2016/155103 A1 | 10/2016 | |
| WO | WO-2016201602 A1 | 12/2016 | |
| WO | WO-2017/015017 A1 | 1/2017 | |
| WO | WO-2017033132 A1 | 3/2017 | |
| WO | WO-2017063535 A1 | 4/2017 | |
| WO | WO-2017113513 A1 | 7/2017 | |
| WO | WO-2017118135 A1 | 7/2017 | |
| WO | WO-2017124334 A1 | 7/2017 | |
| WO | WO-2017156733 A1 | 9/2017 | |
| WO | WO-2017190602 A1 | 11/2017 | |

(56) References Cited

FOREIGN PATENT DOCUMENTS

| | | |
|---|---|---|
| WO | WO-2017/206480 A1 | 12/2017 |
| WO | WO-2018/007633 A1 | 1/2018 |

OTHER PUBLICATIONS

Anonymous: "Newest Hurricane RTA Atomizer Adjustable Airflow E-Phoenix Hurricane RBA Tank VS Fire Bird Goblin Mini Kayfun V3 Mini Vaporizers DHL." Retrieved from the Internet Nov. 16, 2018. URL: https://www.dhgate.com/product/newest-hurricane-rta-atomizer-adjustable/377737091.html.
Anonymous: "China eCig Supplier Elego Wholesale Huge Vapor Starter Kit 2200mah Yocan X-linx." Retrieved from the Internet Nov. 16, 2018. URL: https://www.alibaba.com/product-detail/China-eCig-Supplier-Elego-Wholesale-Huge_60332730872.html?spm=a2700.7724857.normalList.5.785a140b%E2%80%A6.
Anonymous: "ShenRay TAE Adjustable Airflow Atomizer 5ml Capacity Vaporizer 25mm RTA Electronic Cigarette rta Vape." Retrieved from the Internet Nov. 16, 2018. URL: https://www.aliexpress.com/item/ShenRay-TAE-Adjustable-Airflow-Atomizer-5ml-Capacity-Vaporizer-25mm-RTA-Electronic-Cigarette-rta-Vape/328461%E2%80%A6.
Anonymous: "OBS T-VCT Sub Ohm Tank E-Cigarette 6ml RBA Atomizer with 0.25o." Retrieved from the internet Nov. 16, 2018. URL: https://www.gearbest.com/electronic-cigarettes/pp_187373.html.
Anonymous: "SER Little 16mm RDA Atomizer—Silver." Retrieved from the internet Nov. 16, 2018. URL: https://www.gearbest.com/vapor-styles/pp_618116.html.
Anonymous: "Authentic Aspire Mini Nautilus E-Cigarette Atomizer Kit—Silver." Retrieved from the Internet Nov. 16, 2018. URL: https://www.gearbest.com/electronic-cigarettes/pp_104356.html.
International Search Report and Written Opinion thereof dated Feb. 24, 2020 for corresponding International Application No. PCT/EP2019/081972.
International Search Report and Written Opinion thereof dated Feb. 19, 2020 for corresponding International Application No. PCT/EP2019/081987.
International Search Report and Written Opinion thereof dated Feb. 19, 2020 for corresponding International Application No. PCT/EP2019/081985.
International Search Report and Written Opinion thereof dated Feb. 14, 2020 for corresponding International Application No. PCT/EP2019/081970.
Written Opinion dated Oct. 22, 2020 for corresponding International Application No. PCT/EP2019/081985.
U.S. Office Action dated Nov. 5, 2020 for corresponding U.S. Appl. No. 16/196,219.
Written Opinion dated Nov. 3, 2020 for corresponding International Application No. PCT/EP2019/081970.
U.S. Office Action dated Nov. 23, 2020 for corresponding U.S. Appl. No. 16/196,749.
International Preliminary Report on Patentability dated Feb. 16, 2021 for corresponding International Application No. PCT/EP2019/081985.
International Preliminary Report on Patentability dated Mar. 5, 2021 for corresponding International Application No. PCT/EP2019/081970.
U.S. Notice of Allowance dated Apr. 1, 2021 for corresponding U.S. Appl. No. 16/196,219.
U.S. Notice of Allowance dated Apr. 14, 2021 for corresponding U.S. Appl. No. 16/196,749.
U.S. Office Action dated May 10, 2021 for U.S. Appl. No. 16/196,866.
U.S. Notice of Allowance dated Jun. 3, 2021 for corresponding U.S. Appl. No. 16/196,219.
International Preliminary Report on Patentability dated May 25, 2021 for corresponding International Application No. PCT/EP2019/081987.
U.S. Notice of Allowance dated Dec. 29, 2021 for corresponding U.S. Appl. No. 16/196,866.
U.S. Notice of Allowance dated Feb. 17, 2022 for corresponding U.S. Appl. No. 16/196,749.
European Office Action dated Jun. 17, 2022 for corresponding European Application No. 19809744.6.
Japanese Office Action dated Dec. 7, 2023 for corresponding Japanese Application No. 2021-523486, and English-language translation thereof.
U.S. Office Action dated Jan. 29, 2024 for corresponding U.S. Appl. No. 18/348,786.
U.S. Notice of Allowance dated Jul. 10, 2024 for corresponding U.S. Appl. No. 18/348,786.
Russian Notice of Allowance dated Aug. 1, 2023 for corresponding Russian Application No. 2021111752, and English-language translation thereof.
Russian Notice of Allowance dated May 2, 2023 for corresponding Russian Application No. 2021116835, and English-language translation thereof.
Japanese Notice of Allowance dated Jun. 10, 2024 for corresponding Japanese Application No. 2021-523037.
Japanese Notice of Allowance dated Jul. 23, 2024 for corresponding Japanese Application No. 2021-526362.
Japanese Office Action dated Apr. 8, 2024 for corresponding Japanese Application No. 2021-523486.
U.S. Office Action dated May 13, 2024 for corresponding U.S. Appl. No. 17/680,350.
Brazilian Office Action having mailing date of Jul. 4, 2023 for corresponding Brazilian Application No. 1120210087907, and English-language translation thereof.
Chinese Office Action and Search Report dated Sep. 7, 2023 for corresponding Chinese Application No. 201980071056.7, and English-language translation thereof.
Chinese Office Action dated Jun. 9, 2023 for corresponding Chinese Application No. 201980071035.5, and English-language translation thereof.
Japanese Office Action dated Nov. 30, 2023 for corresponding Japanese Application No. 2021-525646, and English-language translation thereof.
Chinese Office Action dated Nov. 30, 2023 for corresponding Chinese Application No. 201980071083.4, and English-language translation thereof.
Japanese Office Action dated Dec. 4, 2023 for corresponding Japanese Application No. 2021-526362, and English-language translation thereof.
Japanese Office Action dated Dec. 4, 2023 for corresponding Japanese Application No. 2021-523037, and English-language translation thereof.
Chinese Office Action dated Oct. 11, 2023 for corresponding Chinese Application No. 201980071064.1, and English-language translation thereof.
U.S. Notice of Allowance dated Mar. 18, 2024 for corresponding U.S. Appl. No. 18/348,786.
Japanese Decision to Grant dated Apr. 22, 2024 for corresponding Japanese Application No. 2021-525646, and English-language translation thereof.
Russian Office Action dated Mar. 1, 2023 for corresponding Russian Application No. 2021111751, and English-language translation thereof.
Russian Office Action and Search Report dated Mar. 1, 2023 for corresponding Russian Application No. 2021111752, and English-language translation thereof.
U.S. Office Action dated Mar. 15, 2023 for corresponding U.S. Appl. No. 17/706,949.
Russian Notice of Allowance dated Jun. 9, 2023 for corresponding Russian Application No. 2021111751, and English-language translation thereof.
U.S. Notice of Allowance dated Jun. 21, 2024 for corresponding U.S. Appl. No. 17/380,350.
Chinese Office Action dated Jun. 5, 2024 for corresponding Chinese Application No. 201980071064.1, and English-language translation thereof.
U.S. Notice of Allowance dated Apr. 5, 2023 for corresponding U.S. Appl. No. 17/706,949.

(56) References Cited

OTHER PUBLICATIONS

Korean Office Action dated Aug. 1, 2024 for corresponding Korean Application No. 10-2021-7016352, and English-language translation thereof.
Korean Office Action dated Aug. 1, 2024 for corresponding Korean Application No. 10-2021-7017498, and English-language translation thereof.
European Communication under Rule 71(3) EPC for corresponding European Application No. 19809744.6, dated Mar. 4, 2024.
Chinese Office Action dated Nov. 22, 2022 for corresponding Chinese Application No. 201980071035.5, and English-language translation thereof.
Russian Office Action and Search Report dated Mar. 9, 2023 for corresponding Russian Application No. 2021116149, and English-language translation thereof.
Russian Notice of Allowance dated Aug. 7, 2023 for corresponding Russian Application No. 2021116149, and English-language translation thereof.
Brazilian Office Action having a mailing date of Aug. 1, 2023 for corresponding Brazilian Application No. 1120210074538, and English-language translation thereof.
Brazilian Office Action having a mailing date of Aug. 1, 2023 for corresponding Brazilian Application No. 1120210072020, and English-language translation thereof.
Korean Notice of Allowance dated Nov. 5, 2024 for corresponding Korean Application No. 10-2021-7016352, and English-language translation thereof.
European Notice of Allowance dated Nov. 7, 2024 for corresponding European Application No. 19809741.2.
Korean Notice of Allowance dated Oct. 11, 2024 for corresponding Korean Application No. 10-2021-7017498, and English-language translation thereof.

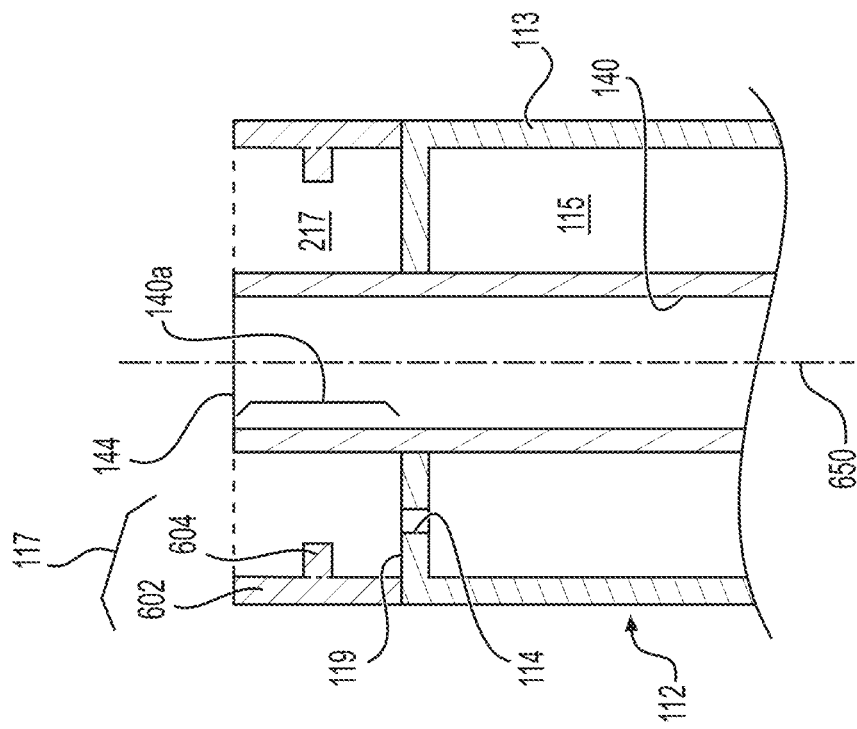
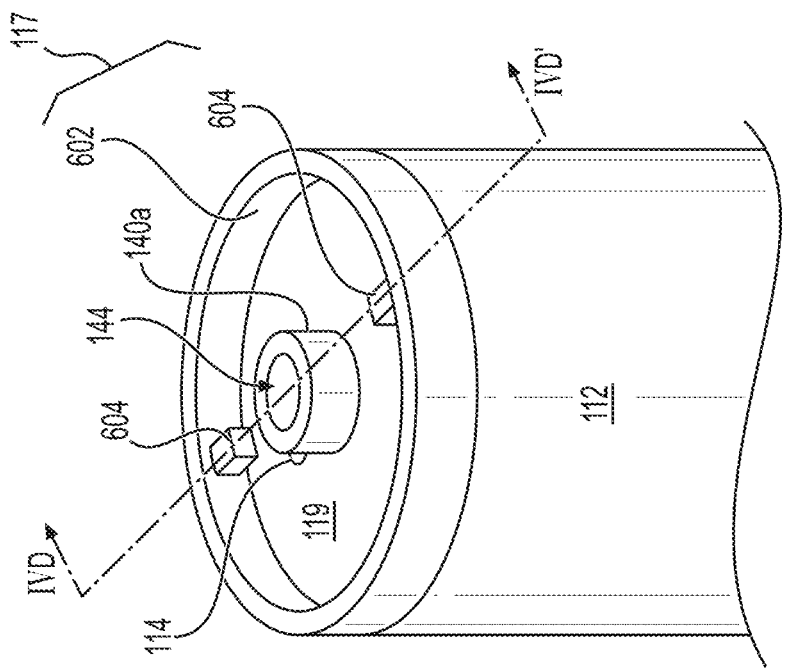

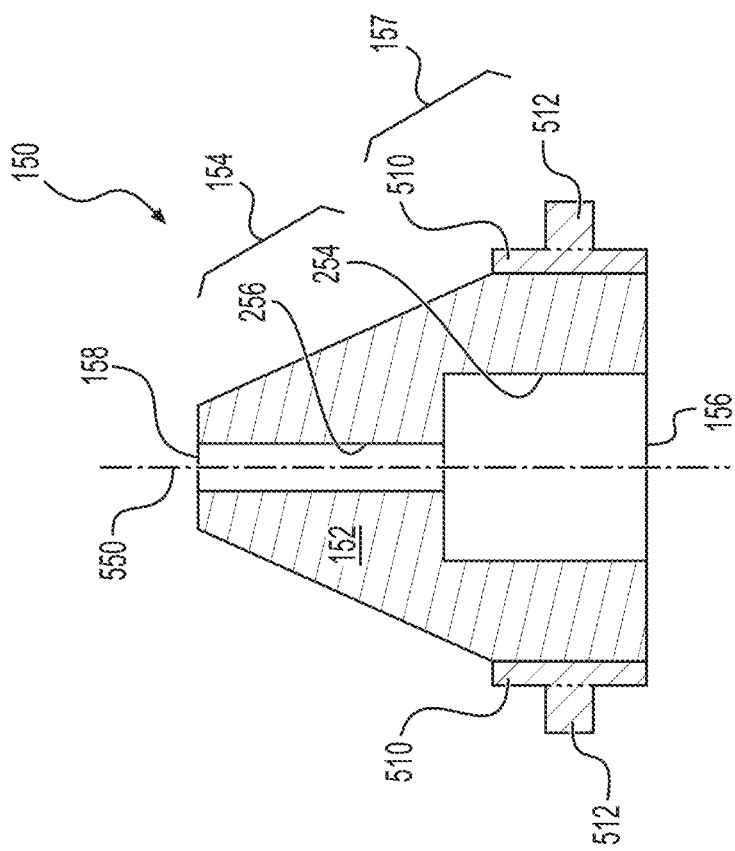
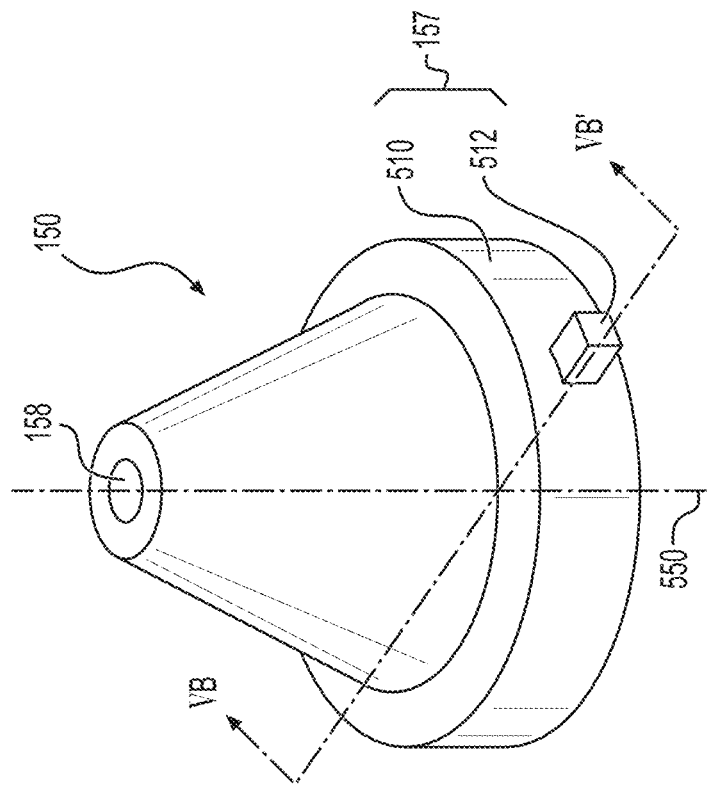
FIG. 5B
FIG. 5A

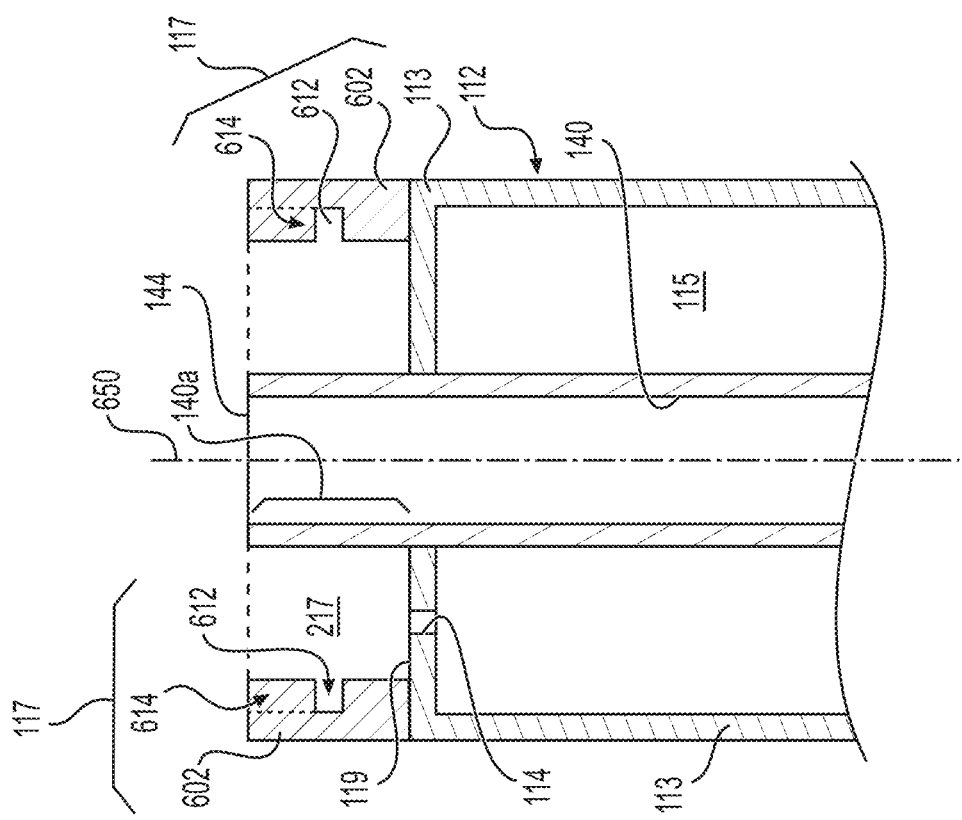
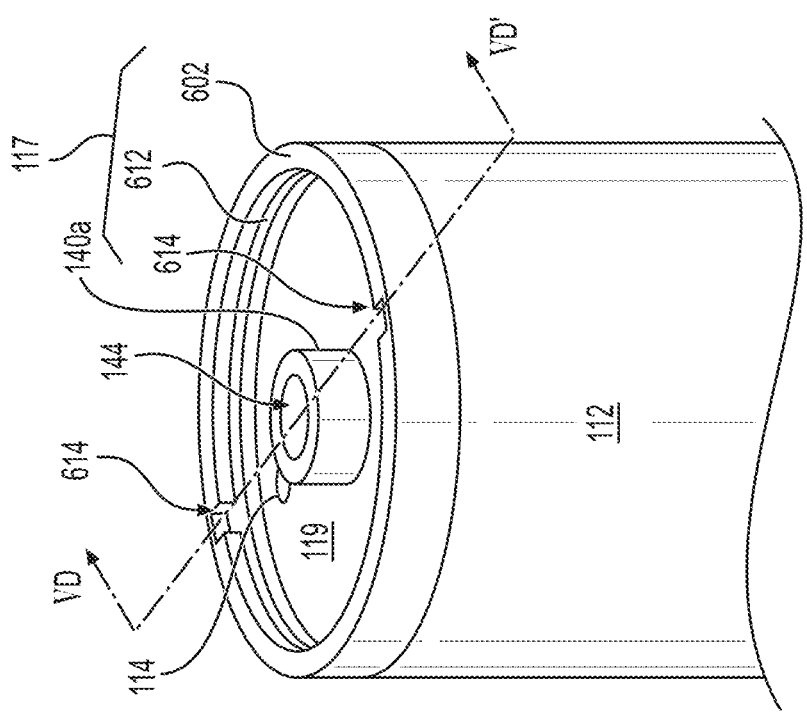
FIG. 5D
FIG. 5C

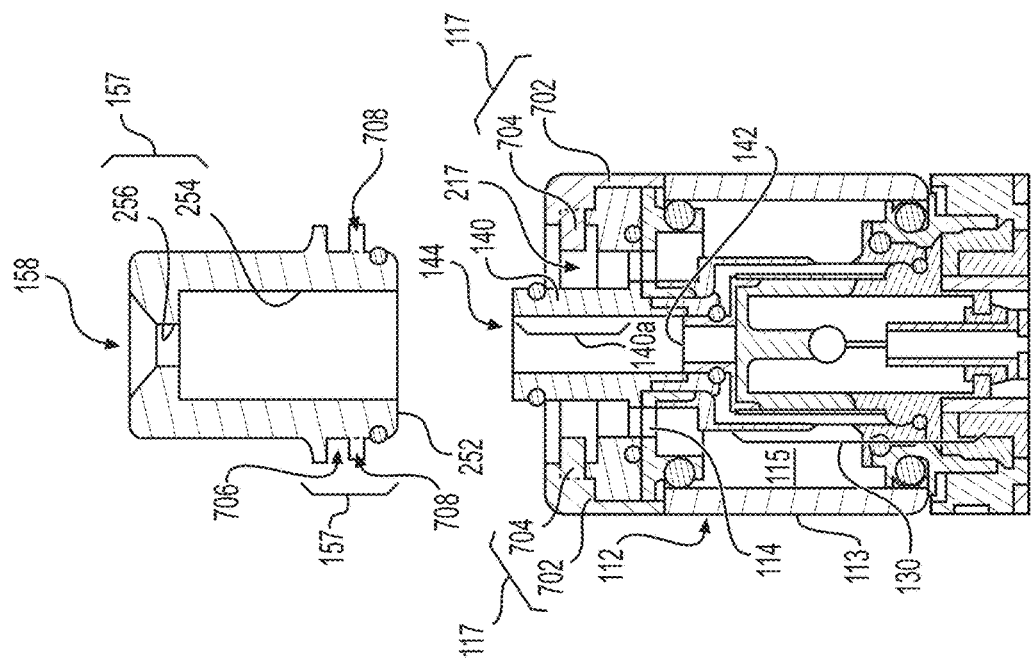
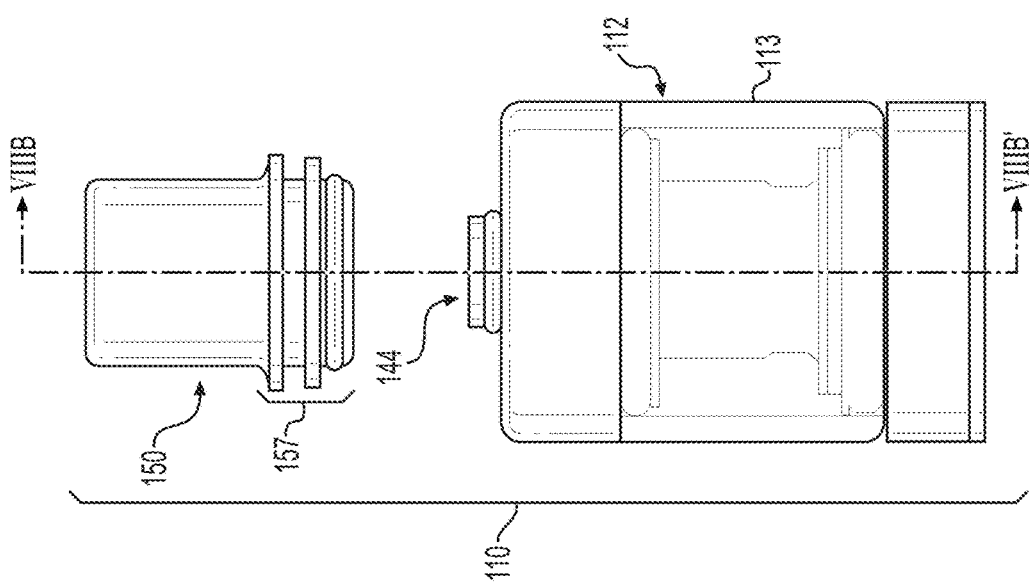
FIG. 8B
FIG. 8A

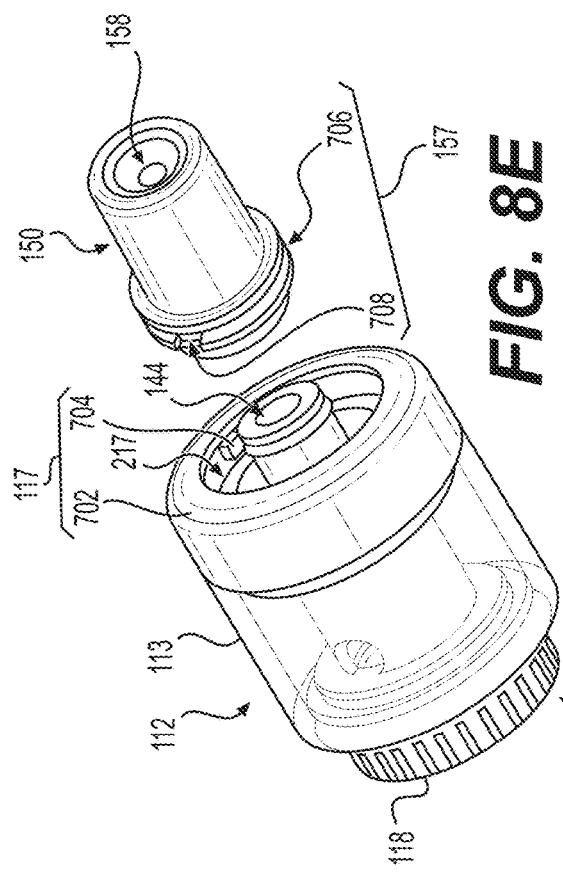
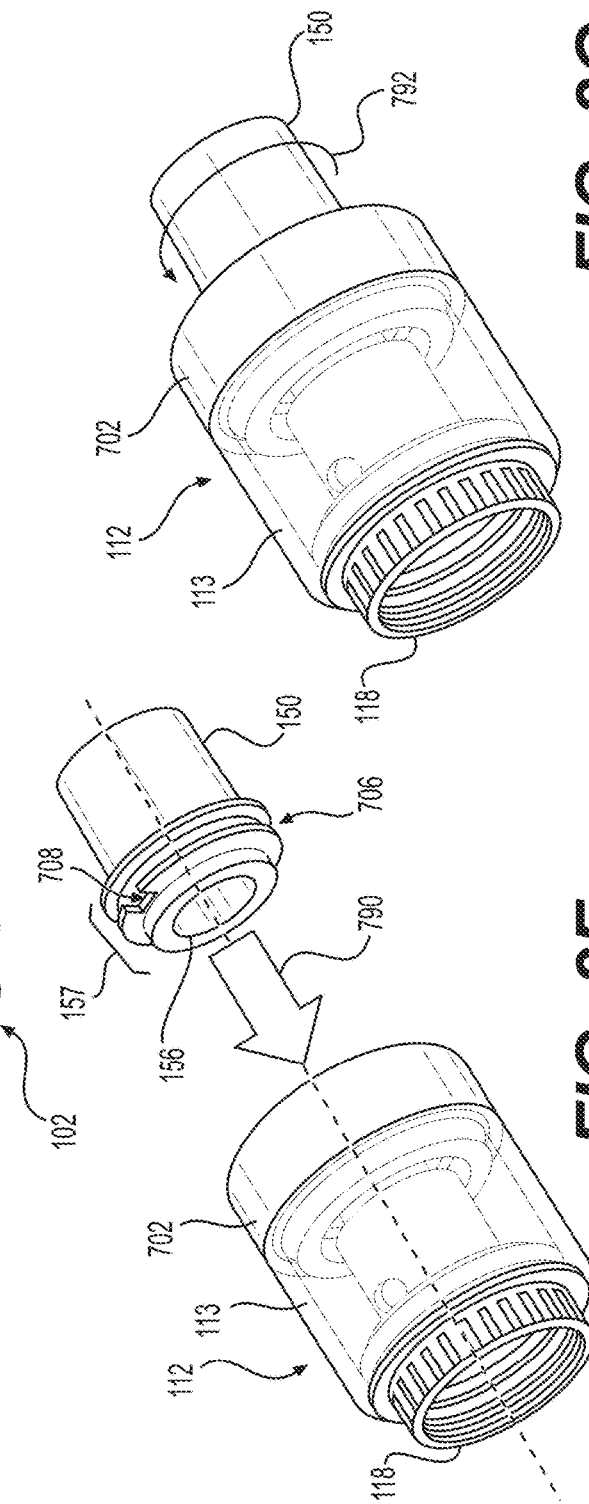

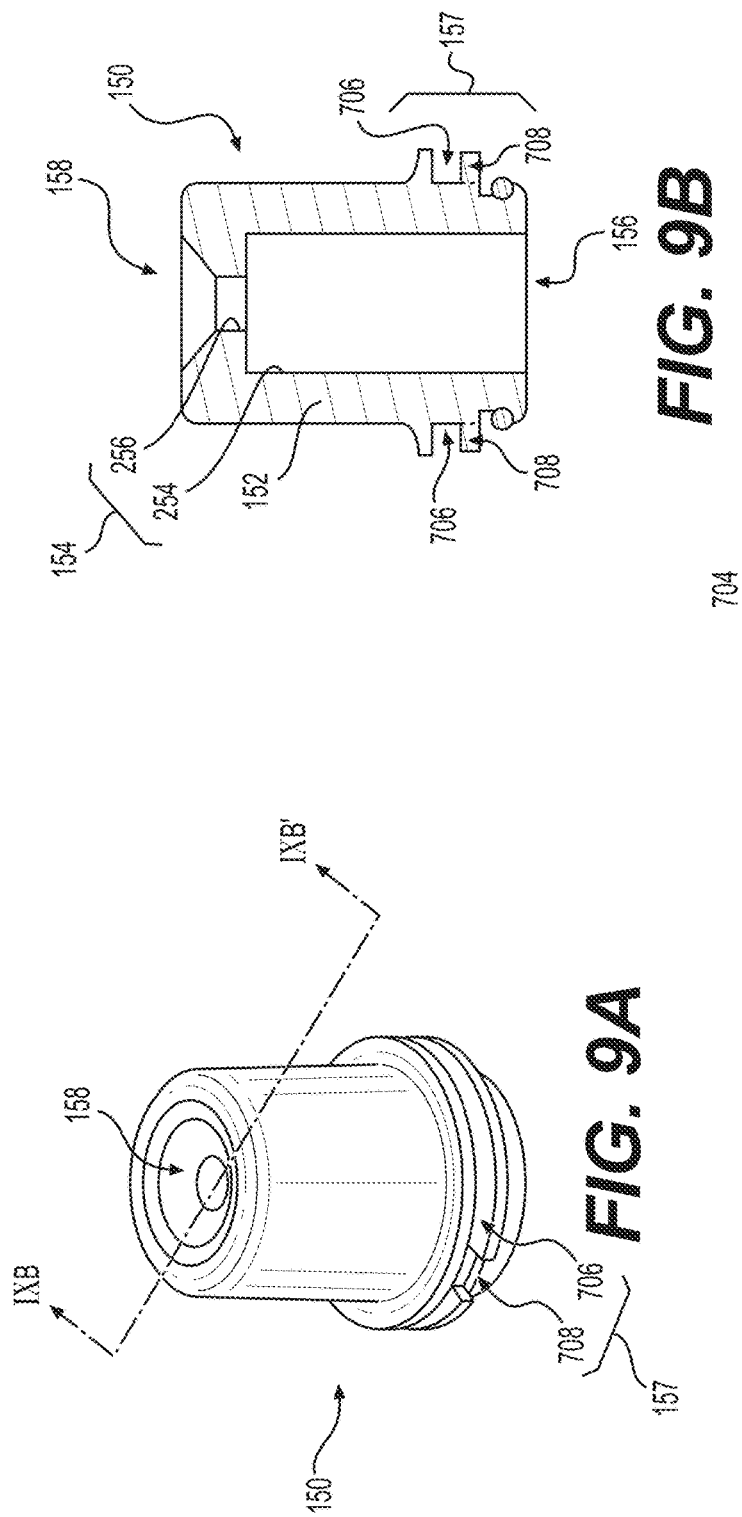

E-VAPING DEVICE

CROSS-REFERENCE TO RELATED APPLICATIONS

This application is a continuation application of U.S. application Ser. No. 16/196,344 filed on Nov. 20, 2018, the entire contents of which are hereby incorporated by reference.

BACKGROUND

Field

Example embodiments relate to electronic vaping devices, e-vaping devices, or the like.

Description of Related Art

E-vaping devices, also referred to herein as electronic vaping devices (EVDs) may be used by adult vapers for fluid portable vaping. An e-vaping device may include a reservoir that holds pre-vapor formulation and a vaporizer assembly that may heat pre-vapor formulation drawn from the reservoir to generate a vapor.

Some e-vaping devices are configured to enable replenishment of the pre-vapor formulation held in a reservoir of the e-vaping device (i.e., refilling of the reservoir).

SUMMARY

According to some example embodiments, a reservoir assembly for an e-vaping device may include a reservoir configured to hold pre-vapor formulation, a first bayonet connector assembly at an end of the reservoir, and a conduit extending into a space defined by the first bayonet connector assembly. The first bayonet connector assembly may be configured to detachably couple with a second bayonet connector assembly of an outlet assembly to establish a bayonet interface connection between the reservoir and the outlet assembly, such that the conduit is in fluid communication with an exterior of the reservoir assembly through an interior of the outlet assembly.

The conduit may extend from a vaporizer assembly.

The vaporizer assembly may be in fluid communication with the exterior of the reservoir assembly through the interior of the outlet assembly when the bayonet interface connection is established.

The reservoir may include a fluid port extending through an outer housing of the reservoir, and wherein the fluid port is isolated from the exterior of the reservoir assembly by the outlet assembly when the bayonet interface connection is established.

The conduit may extend through the space defined by the first bayonet connector assembly.

The first bayonet connector assembly may include a bayonet plug connector element and may be configured to detachably couple with a complementary bayonet receptacle connector element of the second bayonet connector assembly to establish the bayonet interface connection.

The reservoir assembly may further include a vaporizer connector assembly configured to detachably couple the reservoir with the vaporizer assembly.

An end of the conduit may be coupled to the vaporizer connector assembly, such that the conduit is configured to couple with the vaporizer assembly via the vaporizer connector assembly.

The first bayonet connector assembly may be directly coupled to the end of the reservoir.

According to some example embodiments, a vapor generator assembly for an e-vaping device may include a reservoir and a vaporizer assembly, the reservoir configured to supply pre vapor formulation to the vaporizer assembly, a first bayonet connector assembly at an end of the reservoir, and a conduit extending from the vaporizer assembly into a space defined by the first bayonet connector assembly. The conduit may be configured to enable fluid communication between the vaporizer assembly and an exterior of the vapor generator assembly through the first bayonet connector assembly. The vapor generator assembly may include an outlet assembly including a second bayonet connector assembly, the second bayonet connector assembly detachably coupled to the first bayonet connector assembly to establish a bayonet interface connection between the reservoir and the outlet assembly, such that the conduit is in fluid communication with the exterior of the vapor generator assembly through an interior of the outlet assembly.

The vaporizer assembly may be in fluid communication with the exterior of the vapor generator assembly through the interior of the outlet assembly when the bayonet interface connection is established.

The reservoir may include a first fluid port extending through an outer housing of the reservoir. The first fluid port may be isolated from the exterior of the vapor generator assembly by the outlet assembly when the bayonet interface connection is established.

The conduit may extend through the space defined by the first bayonet connector assembly.

The first bayonet connector assembly may include a bayonet plug connector and may be configured to detachably couple with a bayonet receptacle connector of the second bayonet connector assembly to establish the bayonet interface connection.

The vapor generator assembly may include a vaporizer connector assembly, wherein the reservoir is detachably coupled with the vaporizer assembly through the vaporizer connector assembly.

An end of the conduit may be coupled to the vaporizer connector assembly, such that the conduit is coupled with the vaporizer assembly via the vaporizer connector assembly.

The first bayonet connector assembly may be directly coupled to the end of the reservoir.

According to some example embodiments, an e-vaping device may include a vapor generator assembly. The vapor generator assembly may include a reservoir and a vaporizer assembly. The reservoir may be configured to hold pre-vapor formulation. The vaporizer assembly may be configured to heat pre-vapor formulation drawn from the reservoir. The e-vaping device may include a first bayonet connector assembly at an end of the reservoir, and a conduit extending from the vaporizer assembly into a space defined by the first bayonet connector assembly. The e-vaping device may include an outlet assembly including a second bayonet connector assembly. The second bayonet connector assembly may be detachably coupled to the first bayonet connector assembly to establish a bayonet interface connection between the reservoir and the outlet assembly, such that the conduit is in fluid communication with an exterior of the vapor generator assembly through an interior of the outlet assembly. The e-vaping device may include a power supply assembly coupled to the vapor generator assembly. The power supply assembly may include a power supply. The power supply assembly may be configured to supply electrical power from the power supply to the vaporizer assembly of the vapor generator assembly.

The vaporizer assembly may be in fluid communication with the exterior of the vapor generator assembly through the interior of the outlet assembly when the bayonet interface connection is established.

The reservoir may include a first fluid port extending through an outer housing of the reservoir. The first fluid port may be isolated from the exterior of the vapor generator assembly by the outlet assembly when the bayonet interface connection is established.

The conduit may extend through the space defined by the first bayonet connector assembly.

The first bayonet connector assembly may include a bayonet plug connector and may be configured to detachably couple with a bayonet receptacle connector of the second bayonet connector assembly to establish the bayonet interface connection.

The first bayonet connector assembly may be directly coupled to the end of the reservoir.

The power supply assembly may include a rechargeable battery.

The power supply assembly may be detachably coupled with the vapor generator assembly.

The e-vaping device may include a vaporizer connector assembly. The reservoir may be detachably coupled with the vaporizer assembly through the vaporizer connector assembly.

An end of the conduit may be coupled to a vaporizer connector assembly, such that the conduit is coupled with the vaporizer assembly via the vaporizer connector assembly.

BRIEF DESCRIPTION OF THE DRAWINGS

The various features and advantages of the non-limiting example embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 4C is a perspective view of a reservoir assembly according to some example embodiments.

FIG. 4D is a cross-sectional view along line IVD-IVD' of the reservoir assembly of FIG. 4C according to some example embodiments.

FIG. 5A is a perspective view of an outlet assembly according to some example embodiments.

FIG. 5B is a cross-sectional view along line VB-VB' of the outlet assembly of FIG. 5A according to some example embodiments.

FIG. 5C is a perspective view of a reservoir assembly according to some example embodiments.

FIG. 5D is a cross-sectional view along line VD-VD' of the reservoir assembly of FIG. 5C according to some example embodiments.

FIG. 8A is a side view of a reservoir and an outlet assembly decoupled from the reservoir according to some example embodiments.

FIG. 8B is a cross-sectional view along line VIIIB-VIIIB' of the decoupled reservoir and outlet assembly of FIG. 8A according to some example embodiments.

FIG. 8E is a perspective view of the decoupled reservoir and outlet assembly of FIG. 8A according to some example embodiments.

FIG. 8F is a perspective view of the decoupled reservoir and outlet assembly of FIG. 8E according to some example embodiments.

FIG. 8G is a perspective view of a reservoir and an outlet assembly coupled with the reservoir according to some example embodiments.

FIG. 9A is a perspective view of an outlet assembly according to some example embodiments.

FIG. 9B is a cross-sectional view along line IXB-IXB' of the outlet assembly of FIG. 9A according to some example embodiments.

FIG. 9C is a perspective view of a bayonet connector assembly according to some example embodiments.

DETAILED DESCRIPTION OF EXAMPLE EMBODIMENTS

Figure 1A:
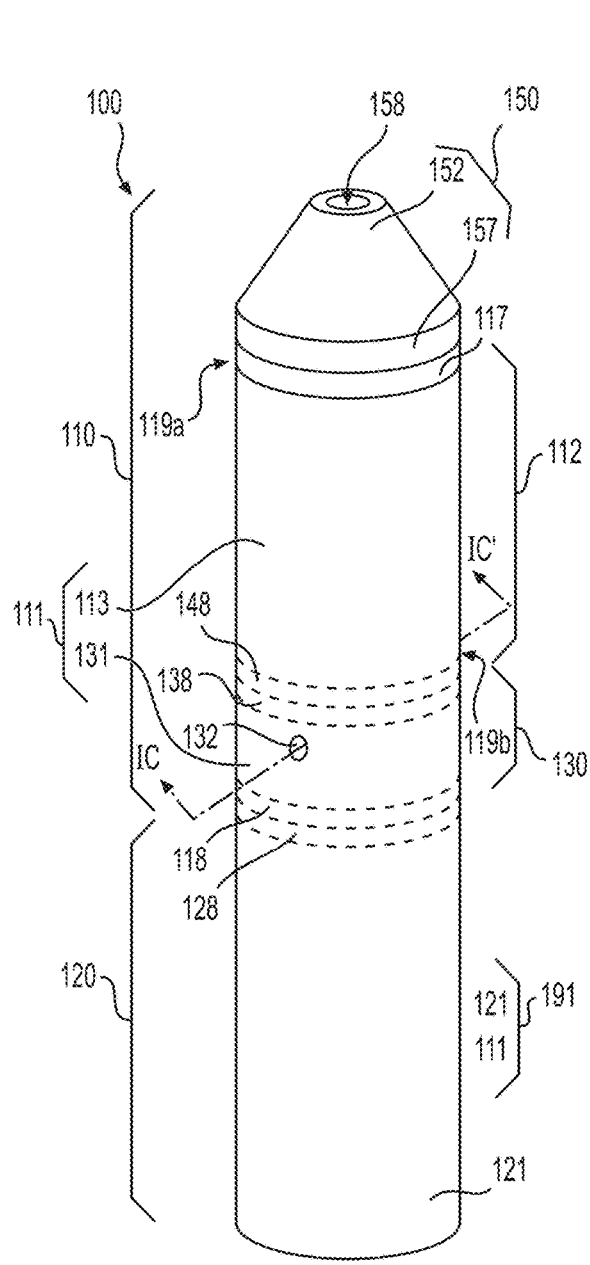
FIG. 1A is a perspective view of an e-vaping device according to some example embodiments.

Some detailed example embodiments are disclosed herein. However, specific structural and functional details disclosed herein are merely provided for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, etc., but do not preclude the presence or addition of one or more other features, integers, steps, operations, elements, etc., and/or groups thereof.

When the words "about" and "substantially" are used in this specification in connection with a numerical value, it is intended that the associated numerical value include a tolerance of ±10% around the stated numerical value, unless otherwise explicitly defined.

Example embodiments are described herein with reference to cross-sectional illustrations that are schematic illustrations of example embodiments. As such, variations from the shapes of the illustrations are to be expected. Thus, example embodiments should not be construed as limited to the shapes of regions illustrated herein but are to include deviations in shapes.

Vapor, aerosol and dispersion are used interchangeably and are meant to cover the matter generated or outputted by the devices disclosed, claimed and/or equivalents thereof.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Hardware may be implemented using processing or control circuitry such as, but not limited to, one or more processors, one or more Central Processing Units (CPUs), one or more microcontrollers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Figure 1B:
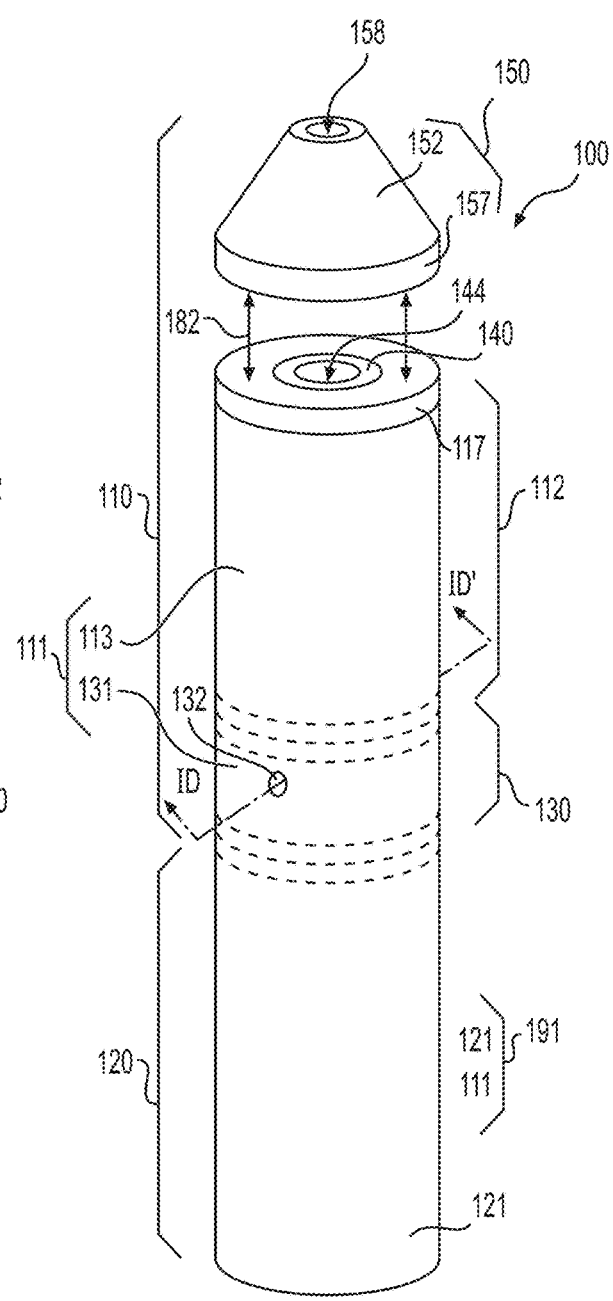
FIG. 1B is a perspective view of an e-vaping device according to some example embodiments.
Figure 1C:
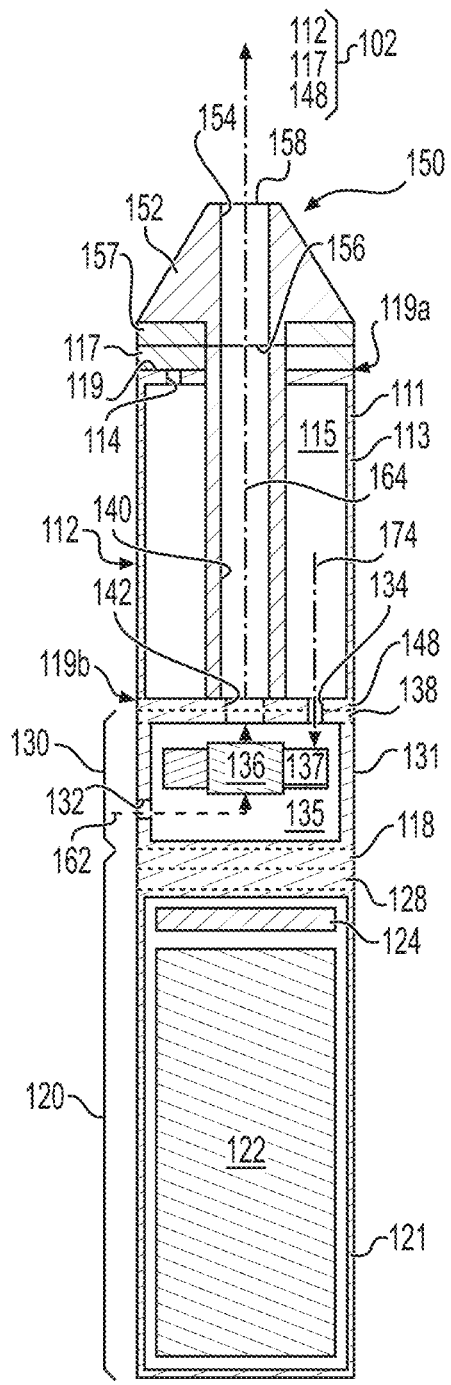
FIG. 1C is a cross-sectional view along line IC-IC' of the e-vaping device of FIG. 1A according to some example embodiments.
Figure 1D:
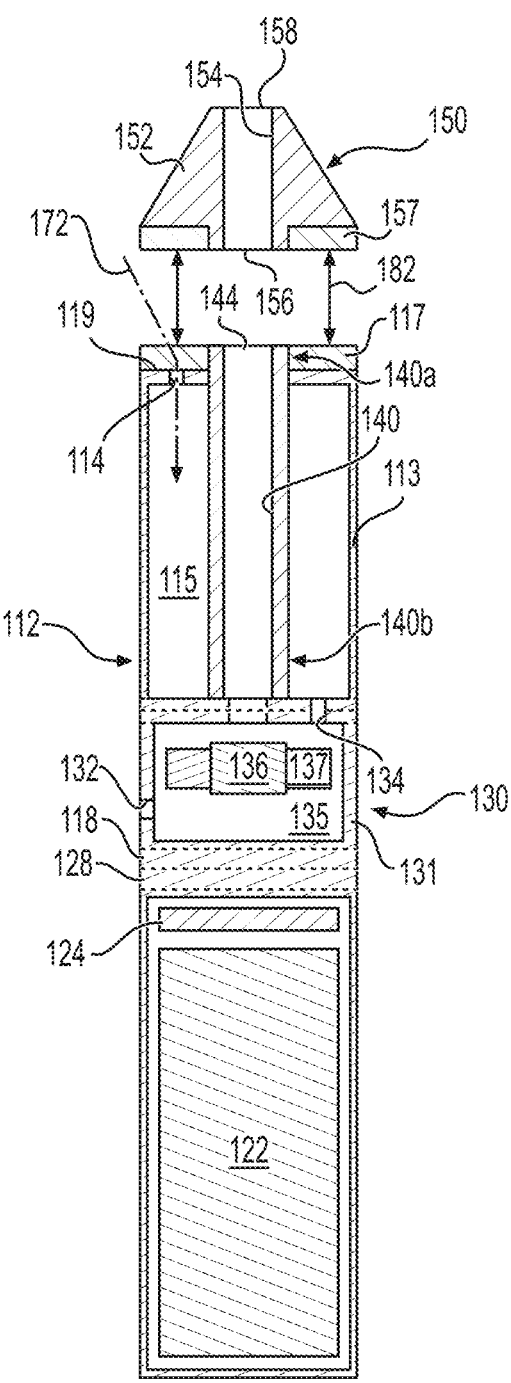
FIG. 1D is a cross-sectional view along line ID-ID' of the e-vaping device of FIG. 1B according to some example embodiments.

FIG. 1A is a perspective view of an e-vaping device 100 according to some example embodiments. FIG. 1B is a perspective view of an e-vaping device 100 according to some example embodiments. FIG. 1C is a cross-sectional view along line IC-IC' of the e-vaping device 100 of FIG. 1A according to some example embodiments. FIG. 1D is a cross-sectional view along line ID-ID' of the e-vaping device 100 of FIG. 1B according to some example embodiments. As used herein, the term "e-vaping device" is inclusive of all types of electronic vaping devices, regardless of form, size or shape.

Referring to FIGS. 1A-1D, the e-vaping device 100 includes a vapor generator assembly 110 and power supply assembly 120. In some example embodiments, a vapor generator assembly 110 that is configured to be detachably coupled to a power supply assembly 120 to form an e-vaping device 100 may be referred to herein as a cartridge.

In some example embodiments, the vapor generator assembly 110 and power supply assembly 120 include respective complementary connector assemblies 118, 128 and are configured to be detachably connected to each other based on detachably coupling the connector assemblies 118, 128 together. In some example embodiments, the connector assemblies 118, 128 include threaded connectors. It should be appreciated that a connector assembly 118, 128 may be any type of connector, including, without limitation, a snug-fit, detent, clamp, bayonet, sliding fit, sleeve fit, alignment fit, threaded connector, magnetic, clasp, or any other type of connection, and/or combinations thereof.

As shown in FIGS. 1A-1D, the vapor generator assembly 110 may include an outer housing 111, and the power supply assembly 120 may include an outer housing 121, where the outer housing 111 and the outer housing 121 may collectively define an outer housing 191 of the e-vaping device 100.

As shown in FIGS. 1A-1D, the vapor generator assembly 110 may include a reservoir 112, a vaporizer assembly 130, a first bayonet connector assembly 117 and an outlet assembly 150, where the outlet assembly 150 includes a second bayonet connector assembly 157. Structures of a first and second bayonet connector assemblies 117, 157 according to example embodiments are described further below with reference to FIGS. 2A-2B, 3A-3B, 4A-4D, 5A-5D, 6A-6C, 7A-7C, 8A-8G, and 9A-9C.

As shown in FIGS. 1A-1D, a reservoir 112, first bayonet connector assembly 117, and vaporizer connector assembly 148 may be included in a reservoir assembly 102 of some example embodiments.

As shown in FIGS. 1A-1D, the outer housing 111 of the vapor generator assembly 110 may include an outer housing 113 of the reservoir 112 and an outer housing 131 of the vaporizer assembly 130, where outer housings 113 and 131 collectively define the outer housing 111. In some example embodiments, housings 113 and 131 are separate connectable housings, and in some example embodiments housings 113 and 131 form part of the same housing. The outer housing 113 of the reservoir 112 may at least partially define an interior space 115. The reservoir 112 may be configured to hold a pre-vapor formulation within the interior of the reservoir 112, where the interior may include the interior space 115 at least partially defined by the outer housing 113 of the reservoir 112.

As shown in at least FIGS. 1C-1D, the reservoir 112 may include a fluid port 114 which extends through the outer housing 113 of the reservoir 112 between the interior space 115 of the reservoir 112 and an exterior of at least the reservoir 112, such that the fluid port 114 is in fluid communication with the exterior of at least the reservoir 112 and thereby may enable fluid communication between the reservoir 112 and the exterior of at least the reservoir 112.

In some example embodiments, the vaporizer assembly 130 and reservoir 112 include respective complementary connector assemblies 138, 148 and are configured to be detachably connected to each other based on detachably coupling the connector assemblies 138, 148 together. For example, the vaporizer connector assembly 148 may be configured to detachably couple the reservoir 112 with the vaporizer assembly 130, for example based on detachably coupling with the connector assembly 138 of the vaporizer assembly 130. In some example embodiments, the connector assemblies 138, 148 include threaded connectors. It should be appreciated that a connector assembly 138, 148 may be any type of connector, including, without limitation, a snug-fit, detent, clamp, bayonet, sliding fit, sleeve fit, alignment fit, threaded connector, magnetic, clasp, or any other type of connection, and/or combinations thereof.

As shown in at least FIGS. 1C-1D, the vaporizer assembly 130 may include an outer housing 131 that at least partially defines an interior space 135 of the vaporizer assembly 130. As further shown in at least FIGS. 1C-1D, the vaporizer assembly 130 may include a fluid port 134 which extends through the outer housing 131 of the vaporizer assembly 130 between the interior space 135 of the vaporizer assembly 130 and an exterior of the vaporizer assembly 130, such that the fluid port 134 may enable fluid communication between the interior space 135 and an exterior of the vaporizer assembly 130. As further shown in FIG. 1B, the fluid port 134 may enable fluid communication between the reservoir 112 and the vaporizer assembly 130. In some example embodiments, the fluid port 134 extends through the outer housing 113 of the reservoir 112, in addition to or instead of extending through the outer housing 131 of the vaporizer assembly 130. In some example embodiments, where housing 113 meets with housing 131 may form part of the same housing, or these may be two separate housings that can be connected together (e.g., via complementary connector assemblies 138, 148). In some example embodiments, fluid port 114 may include more than one port (e.g., there may be multiple first fluid ports), and/or fluid port 134 may include more than one port (e.g., there may be multiple second fluid ports).

The vaporizer assembly 130 may include a heater 136 and a dispensing interface 137. The dispensing interface 137 may be in fluid communication with the fluid port 134 and in fluid communication with the reservoir 112 through at least the fluid port 134, and pre-vapor formulation 174 drawn into the interior space 135 through fluid port 134 may be drawn by the dispensing interface 137 to be in fluid communication with the heater 136. The heater 136 (also referred to herein as a heating element) may heat pre-vapor formulation drawn from the reservoir 112 by the dispensing interface (e.g., through the fluid port 134) to generate a vapor.

As further shown in FIGS. 1A-1D, the vapor generator assembly 110 may include an inlet port 132 that extends through the outer housing 131 of the vaporizer assembly 130 and is configured to direct air from an exterior of the vapor generator assembly 110 (e.g., an ambient environment) to flow into the vaporizer assembly 130, to flow in fluid communication with the heater 136 within at least a portion of the interior space 135 of the vaporizer assembly 130. As further shown in FIGS. 1A-1D, the vaporizer assembly 130 may include an outlet port 142 extending through the outer housing 131 of the vaporizer assembly 130 and the vapor generator assembly 110 may further include a conduit 140 coupling outlet ports 142, 144 to establish fluid communication between the vaporizer assembly 130 and the exterior of the vapor generator assembly 110 (e.g., the ambient environment).

In operation of the e-vaping device 100, air 162 may be drawn into the vaporizer assembly 130 through at least the inlet port 132, vapor generated by the heater 136 may be entrained in the air that is drawn into the vaporizer assembly 130, and a mixture of the air and entrained vapor (simply referred to herein as generated vapor 164) may be drawn from the vaporizer assembly 130 to the exterior of the vapor generator assembly 110 through outlet port 142, conduit 140, and outlet port 144. As shown in FIGS. 1A-1D, the outlet port 142 may extend through the outer housing 131 of the vaporizer assembly 130, the outer housing 113 of the reservoir 112, a vaporizer connector assembly 148, a connector assembly 138, a sub-combination thereof, or a combination thereof.

In some example embodiments, reservoir assembly 102 is configured to enable refilling of the pre-vapor formulation held in reservoir 112. As shown in FIGS. 1C-1D, the fluid port 114 may enable direct fluid communication between the reservoir 112 and an exterior of at least the reservoir 112. Thus, the reservoir assembly 102 may be configured to enable refilling of the reservoir 112 via introduction of pre-vapor formulation 172 into the reservoir 112 through at least the fluid port 114.

Still referring to FIGS. 1A-1D, the reservoir assembly 102 may include a first bayonet connector assembly 117 that is coupled to a first end 119a of the reservoir 112. The first bayonet connector assembly 117 may include a bayonet plug connector element (also referred to as a male bayonet connector element), a bayonet receptacle connector element (also referred to as a female bayonet connector element), or both a bayonet plug connector element and a bayonet receptacle connector element. Additionally, as shown in FIGS. 1C-1D, the fluid port 114 may extend through the outer housing 113 of the reservoir 112 to an outer surface 119 of the outer housing 113 at the first end 119a of the reservoir 112.

As further shown in FIGS. 1C-1D, the conduit 140 may include a first end 140a and a second end 140b that extend to opposite first and second ends 119a, 119b of the reservoir 112, where the first end 140a of the conduit 140 extends into the first bayonet connector assembly 117 and the second end 140b of the conduit 140 is coupled with the vaporizer assembly 130 (either directly or indirectly via at least a vaporizer connector assembly 148). Accordingly, the conduit 140 may establish fluid communication between the vaporizer assembly 130 and the exterior of the vapor generator assembly 110 through the first bayonet connector assembly 117. As shown, the first end 140a of the conduit 140 may include an opening that is defined as the outlet port 144, and the second end 140b of the conduit 140 may include an opening that is in fluid communication with outlet port 142. In some example embodiments, the first bayonet connector assembly 117 is directly coupled to the first end 140a of the conduit 140. In some example embodiments, where the vapor generator assembly 110 includes the vaporizer connector assembly 148 and the connector assembly 138, the second end 140b of the conduit 140 may be coupled to the vaporizer connector assembly 148, such that the second end 140b of the conduit 140 is configured to couple with the vaporizer assembly 130 through the vaporizer connector assembly 148.

Still referring to FIGS. 1A-1D, the vapor generator assembly 110 may include an outlet assembly 150 (also referred to herein as a mouthpiece, mouthpiece assembly, or the like) that is configured to be detachably coupled 182 to the reservoir 112 via a bayonet interface connection between the reservoir 112 and the outlet assembly 150. As shown, the outlet assembly 150 may include an instance of structural material 152, a conduit 154 extending through the interior of the outlet assembly 150 (e.g., through the instance of structural material 152 such that one or more inner surfaces of the instance of structural material 152 may at least partially define the conduit 154) between opposite openings 156, 158, and a second bayonet connector assembly 157. The second bayonet connector assembly 157 may include a bayonet plug connector element (also referred to as a male bayonet connector element), a bayonet receptacle connector element (also referred to as a female bayonet connector), or both a bayonet plug connector element and a bayonet receptacle connector element. As shown in FIGS. 1A-7A, in some example embodiments the structural material 152 of the outlet assembly 150 may define a conical shape, but example embodiments are not limited thereto. For example, as shown in FIGS. 8A-9C, the outlet assembly 150 may include an instance of structural material that defines an outer surface having a cylindrical shape.

As shown in FIGS. 1A-1D, the first and second bayonet connector assemblies 117, 157 may be configured to be detachably coupled with each other to establish a bayonet interface connection between at least the reservoir 112 and the outlet assembly 150, such that the conduit 140 is in fluid communication with an exterior of at least the reservoir 112 through an interior of the outlet assembly (e.g., through conduit 154), and the fluid port 114 is isolated from an exterior of at least the reservoir 112 by at least a portion of the outlet assembly 150 to isolate the reservoir 112 from fluid communication with the exterior of at least the reservoir 112 (independently of at least the vaporizer assembly 130). In some example embodiments, the fluid port 114 is configured to be isolated from the exterior of at least the reservoir 112 by at least a portion of the structural material 152 of the outlet assembly 150, at least a portion of the second bayonet connector assembly 157 of the outlet assembly 150, or a combination thereof, based on the outlet assembly 150 being detachably coupled with the reservoir 112 via the bayonet interface connection established via the coupling of the first and second bayonet connector assemblies 117, 157.

Based on the outlet assembly 150 isolating the fluid port 114 based on being detachably coupled with the reservoir 112 via the detachable coupling of the first and second bayonet connector assemblies 117, 157, the transfer of pre-vapor formulation 172 between the reservoir 112 and an exterior of at least the reservoir 112 independently of passing through the vaporizer assembly 130 may be at least partially mitigated. To enable refilling of the pre-vapor formulation 172 in the reservoir 112 via the fluid port 114, the outlet assembly 150 may be detached from the reservoir 112 (via decoupling of the first and second bayonet connector assemblies 117, 157) to expose the fluid port 114 to an exterior of at least the reservoir 112.

In some example embodiments, the first and second bayonet connector assemblies 117, 157 include complementary bayonet connector elements. For example, the first bayonet connector assembly 117 may include a bayonet plug connector element and the second bayonet connector assembly 157 may include a bayonet receptacle connector element that is complementary to the bayonet plug connector element of the first bayonet connector assembly 117, such that at least the first and second bayonet connector assemblies 117, 157 are understood to be complementary with respect to each other and thus at least the first bayonet connector assembly 117 is configured to detachably couple with the second bayonet connector assembly 157 to establish the bayonet interface connection between the reservoir 112 and the outlet assembly 150 based on the detachably coupling of the complementary bayonet connector elements of the first and second bayonet connector assemblies 117, 157.

In some example embodiments, the vapor generator assembly 110 is configured to provide improved resistance against transfer of pre-vapor formulation 172 from the reservoir 112 to an exterior of at least the reservoir 112 through the fluid port 114 based on the outlet assembly 150 being detachably coupled to at least the reservoir 112 via a bayonet interface connection established by the first bayonet connector assembly 117 coupling with the second bayonet connector assembly 157. In certain example embodiments, the bayonet interface connection may provide improved isolation of the fluid port 114 from the exterior of at least the reservoir 112 in relation to other interface connections, including, without limitation, a threaded interface connection.

Still referring to FIGS. 1A-1D, a power supply assembly 120 according to some example embodiments may include a power supply 122. The power supply 122 may be a rechargeable battery, and the power supply assembly 120 may be configured to supply electrical power from the power supply 122 to the vapor generator assembly 110 (e.g., to the heater 136 via one or more electrical leads) to support vapor generation at the vaporizer assembly 130.

As shown in FIGS. 1C-1D, an e-vaping device 100 according to some example embodiments may include an instance of control circuitry 124 that may be configured to control the supply of electrical power from the power supply 122 to the vapor generator assembly 110 (e.g., to the vaporizer assembly 130). In the example embodiments shown in FIGS. 1C-1D, the control circuitry 124 is included in the power supply assembly 120, but it will be understood that, in some example embodiments, the control circuitry 124 may be included in the vapor generator assembly 110 instead of the power supply assembly 120.

In some example embodiments, wherein the vapor generator assembly 110 and the power supply assembly 120 are configured to be detachably coupled via complementary connector assemblies 118 and 128, respectively, one or more electrical circuits through the vapor generator assembly 110 and the power supply assembly 120 may be established based on connector assemblies 118, 128 being coupled together. The established electrical circuits may include at least the heater 136, the control circuitry 124, and the power supply 122. The electrical circuit may include one or more electrical leads in one or both of connector assemblies 118, 128.

In some example embodiments, the e-vaping device 100 may be a unitary piece that includes the vapor generator assembly 110 and the power supply assembly 120 in the unitary piece, instead of including the vapor generator assembly 110 and the power supply assembly 120 as separate pieces that are coupled together to form the e-vaping device 100.

In some example embodiments, the power supply 122 may include a battery. In some examples, the power supply 122 may be a Lithium-ion battery or one of its variants, for example a Lithium-ion polymer battery, a nickel-metal hydride battery, a nickel cadmium battery, a lithium-manganese battery, a lithium-cobalt battery, a fuel cell, etc., a sub-combination thereof, or a combination thereof. The e-vaping device 100 may be usable by an adult vaper until the energy in the power supply 122 is depleted or a minimum voltage cut-off level is achieved. Further, the power supply 122 may be rechargeable and may include circuitry configured to allow the battery to be chargeable by an external charging device. To recharge the e-vaping device 100, a Universal Serial Bus (USB) charger or other suitable charger assembly may be used.

In some example embodiments, the power supply 122 may be electrically connected with the heater 136 by control circuitry 124 based on a signal received at the control circuitry 124 from a sensor of the e-vaping device 100, an interface of the e-vaping device 100, or a combination thereof. To control the supply of electrical power to a heater 136, the control circuitry 124 may execute one or more instances of computer-executable program code. The control circuitry 124 may include a processor and a memory. The memory may be a computer-readable storage medium storing computer-executable code. The control circuitry 124 may be a special purpose machine configured to execute the computer-executable code to control the supply of electrical power to the heater 136.

In some example embodiments, connector assemblies 118, 128 are omitted from the e-vaping device 100, such that the vapor generator assembly 110 and the power supply assembly 120 are fixedly coupled together (e.g., are integral to each other) and are precluded from being detachably coupled with each other, and the outer housing 191 of the e-vaping device 100 may include the outer housing 111 of the vapor generator assembly 110 and the outer housing 121 of the power supply assembly 120 as a unitary piece of material.

In some example embodiments, connector assemblies 138, 148 are omitted from the vapor generator assembly 110, such that the reservoir 112 and the vaporizer assembly 130 are fixedly coupled together (e.g., are integral to each other) and are precluded from being detachably coupled with each other, and the outer housing 111 of the vapor generator assembly 110 may include the outer housing 113 of the reservoir 112 and the outer housing 131 of the vaporizer assembly as a unitary piece of material.

The exterior of at least the reservoir 112 may include an exterior of the reservoir 112, an exterior of the reservoir assembly 102, an exterior of the vapor generator assembly 110, an exterior of the e-vaping device 100, a sub-combination thereof, or a combination thereof. Accordingly, an exterior of at least the reservoir 112 may include an external environment that is external to the reservoir 112, an external environment that is external to the reservoir assembly 102, an external environment that is external to the vaporizer assembly 130, an external environment that is external to the vapor generator assembly 110, an external environment that is external to the e-vaping device 100, a sub-combination thereof, or a combination thereof.

The pre-vapor formulation is a material or combination of materials that may be transformed into a vapor. In some example embodiments, one or more portions of the vapor generator assembly 110 may be replaceable. Such one or more portions may include the vaporizer assembly 130, the reservoir 112, the reservoir assembly 102, the power supply assembly 120, the outlet assembly 150, a sub-combination thereof, or a combination thereof. In some example embodiments, the entire e-vaping device 100 may be disposed once the reservoir 112, the vaporizer assembly 130, or a combination thereof is depleted.

Figures 2A, 2B:
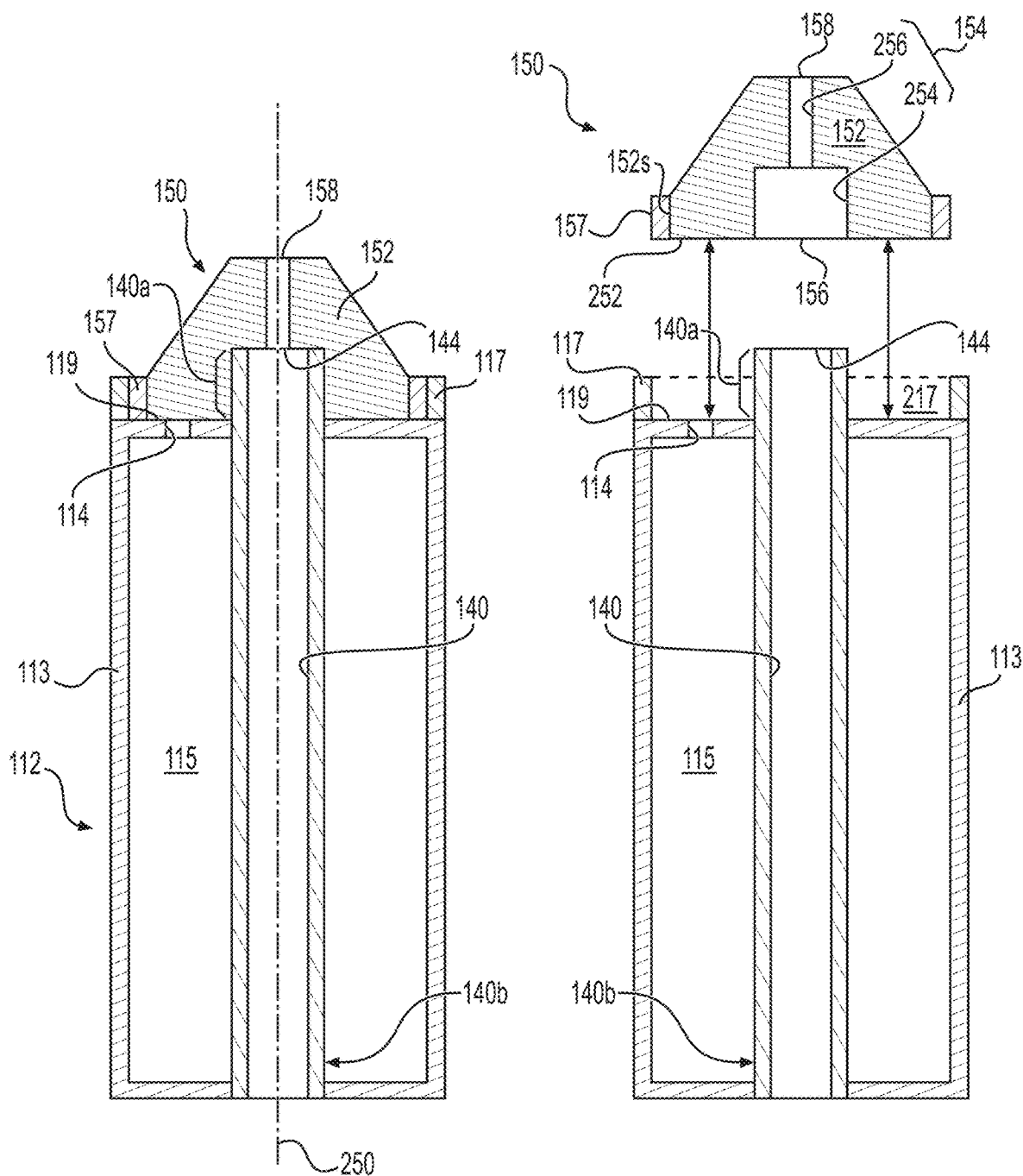
FIG. 2A is a cross-sectional view of a portion of a vapor generator assembly that includes a reservoir coupled with an outlet assembly according to some example embodiments.
FIG. 2B is a cross-sectional view of a portion of a vapor generator assembly that includes a reservoir decoupled from an outlet assembly according to some example embodiments.
Figure 3A:
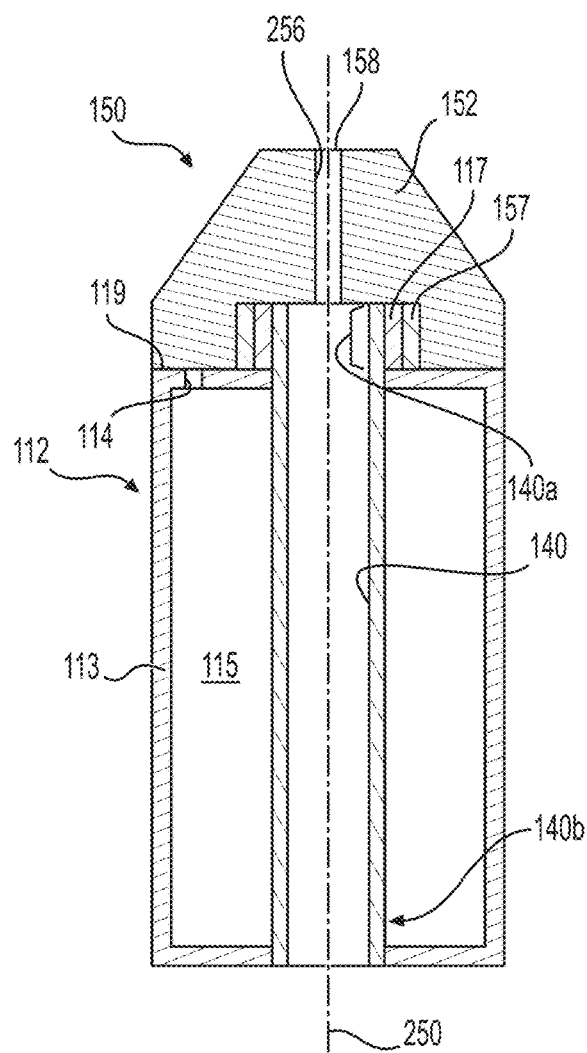
FIG. 3A is a cross-sectional view of a portion of a vapor generator assembly that includes a reservoir coupled with an outlet assembly according to some example embodiments.
Figure 3B:
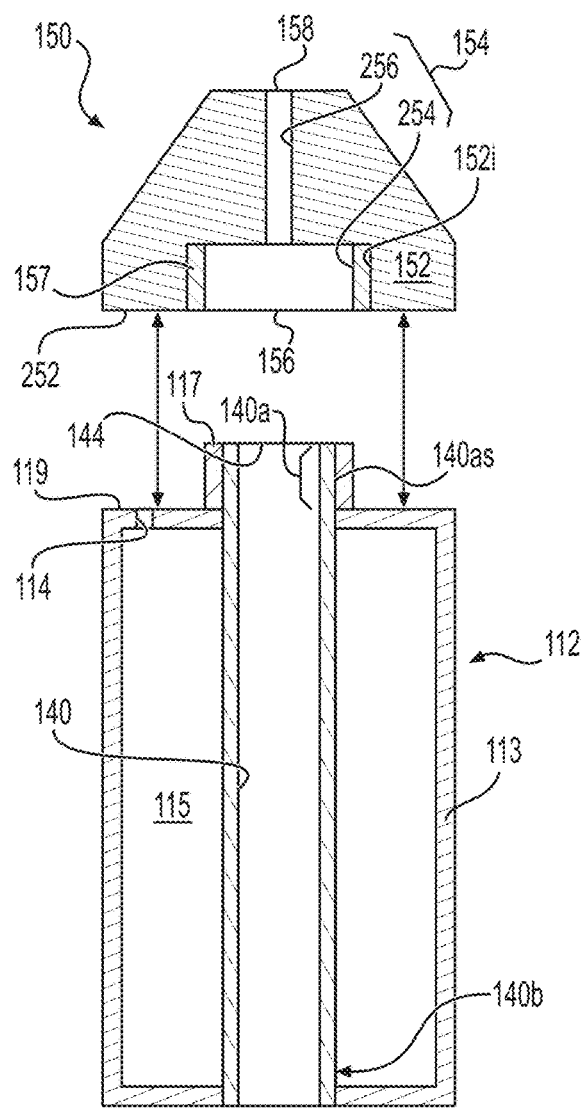
FIG. 3B is a cross-sectional view of a portion of a vapor generator assembly that includes a reservoir decoupled from an outlet assembly according to some example embodiments.

FIG. 2A is a cross-sectional view of a portion of a vapor generator assembly 110 that includes a reservoir 112 coupled with an outlet assembly 150 according to some example embodiments. FIG. 2B is a cross-sectional view of a portion of a vapor generator assembly 110 that includes a reservoir 112 decoupled from an outlet assembly 150 according to some example embodiments. FIG. 3A is a cross-sectional view of a portion of a vapor generator assembly 110 that includes a reservoir 112 coupled with an outlet assembly 150 according to some example embodiments. FIG. 3B is a cross-sectional view of a portion of a vapor generator assembly 110 that includes a reservoir 112 decoupled from an outlet assembly 150 according to some example embodiments.

In some example embodiments, including the example embodiments shown in FIGS. 2A-2B, the first bayonet connector assembly 117 may extend around an outer circumference of an outer surface 119 of the outer housing 113 of the reservoir 112, at the first end 119a of the reservoir 112, such that the first bayonet connector assembly 117 includes one or more bayonet connector elements that face radially inward toward the longitudinal axis 250, and first bayonet connector assembly 117 and the outer surface 119 at least partially define a partial enclosure 217, and the second bayonet connector assembly 157 may extend around an outer surface 152s of the structural material 152 of the outlet assembly 150, such that the second bayonet connector assembly 157 includes one or more bayonet connector elements that face radially outward from the longitudinal axis 250. Examples of first bayonet connector assemblies 117 and second bayonet connector assemblies 157 according to example embodiments are further described below. As shown in FIGS. 2A-2B, when first and second bayonet connector assemblies 117, 157 are coupled together to establish a bayonet interface connection between the reservoir 112 and the outlet assembly 150, the radially-outward facing bayonet connector element(s) of the second bayonet connector assembly 157 may engage with the complementary and radially-inward facing bayonet connector element(s) of the first bayonet connector assembly 117, and at least a portion of the second bayonet connector assembly 157 and the structural material 152 of the outlet assembly 150 may occupy the partial enclosure 217.

As shown in FIGS. 2A-2B, the fluid port 114 may extend through the outer housing 113 of the reservoir 112 to the outer surface 119, such that the fluid port 114 may be in direct fluid communication with the partial enclosure 217 when the outlet assembly 150 is decoupled from the reservoir 112. Still referring to FIGS. 2A-2B, at least the first end 140a of the conduit 140 may extend out of the reservoir 112 and at least partially through the partial enclosure 217 that is at least partially defined by the first bayonet connector assembly 117 and the outer surface 119. As shown in FIGS. 2A-2B, the outlet assembly 150 conduit 154 may include a first portion 254, defined by inner surfaces of the structural material 152 of the outlet assembly 150, that has a first diameter and a first length that substantially corresponds (e.g., corresponds within manufacturing tolerances and/or material tolerances) to a diameter and length of the first end 140a of the conduit 140. Accordingly, as shown in FIGS. 2A-2B, the outlet assembly 150 may enclose the first end 140a of the conduit 140 that extends out of the reservoir 112 and at least partially through the partial enclosure 217 within the first portion 254 of the conduit 154, based on the outlet assembly 150 being detachably coupled to the reservoir 112. As further shown in FIGS. 2A-2B, the conduit 154 may include a second portion 256 in addition to the first portion 254, where the first portion 254 and the second portion 256 have a different diameters and/or different lengths.

In certain example embodiments, such an enclosure of the first end 140a of the conduit 140 may establish an airtight or substantially airtight seal between the conduit 140 and the outlet assembly 150. In some example embodiments, the conduit 140 is in fluid communication with the exterior of at least the reservoir assembly 102 through the conduit 154 that extends through the interior of the outlet assembly 150. Accordingly, when generated vapor 164 is directed through conduit 140 from a vaporizer assembly 130, the generated vapor 164 may be directed from the conduit 140 to the exterior of the vapor generator assembly 110 through the interior of the outlet assembly 150 (e.g., conduit 154).

Still referring to FIGS. 2A-2B, the structural material 152 of the outlet assembly 150 may define a bottom surface 252 of the outlet assembly 150. The outlet assembly 150 may be configured to detachably couple with at least the reservoir 112, based on the first and second bayonet connector assemblies 117, 157 coupling with each other, such that at least a portion of the second bayonet connector assembly 157, the structural material 152 of the outlet assembly 150, or a combination thereof may occupy the partial enclosure 217 and the bottom surface 252 may cover the fluid port 114 extending through the outer surface 119 of the reservoir 112, thereby isolating the reservoir 112 from fluid communication with an exterior of the reservoir assembly 102 independently of the vaporizer assembly 130.

In some example embodiments, including the example embodiments shown in FIGS. 3A-3B, the second bayonet connector assembly 157 may be at least partially located within the interior of the outlet assembly 150 and may extend around an inner surface 152i of the structural material 152 to at least partially define a first portion 254 of the conduit 154 extending through the outlet assembly 150, and the first bayonet connector assembly 117 that is complementary to the second bayonet connector assembly 157 may extend around an outer surface 140as of the first end 140a of the conduit 140, such that the first bayonet connector assembly 117 includes one or more bayonet connector elements that face radially outward from the longitudinal axis 250 and such that the first end 140a of the conduit 140 extends through the first bayonet connector assembly 117. Examples of first bayonet connector assemblies 117 and second bayonet connector assemblies 157 according to example embodiments are further described below.

In some example embodiments, each bayonet connector assembly of the first and second bayonet connector assemblies 117, 157 may include multiple bayonet connector sub-assemblies that each include one or more bayonet connector elements. As a result, detachably coupling the outlet assembly 150 with the reservoir 112 may include detachably coupling multiple bayonet connector sub-assemblies of the first bayonet connector assembly 117 with separate, respective complementary bayonet connector sub-assemblies of the second bayonet connector assembly 157 to establish multiple bayonet interface connections between the outlet assembly 150 and the reservoir 112. In some example embodiments, each bayonet connector assembly of the first and second bayonet connector assemblies 117, 157 may include multiple bayonet connector sub-assemblies that each include one or more bayonet connector elements, based on a combination of the embodiments of the bayonet connector assemblies shown in FIGS. 2A-2B and FIGS. 3A-3B. Accordingly, in such example embodiments, the first bayonet connector assembly 117 may include both a bayonet connector sub-assembly that may extend around an outer circumference of an outer surface 119 of the outer housing 113 of the reservoir 112, at the first end 119a of the reservoir 112, similarly to the first bayonet connector assembly 117 of FIGS. 2A-2B, and another bayonet connector sub-assembly that extends around an outer surface 140as of the first end 140a of the conduit 140, similarly to the first bayonet connector assembly 117 of FIGS. 3A-3B. Additionally, in such example embodiments, the second bayonet connector assembly 157 may include both a bayonet connector sub-assembly that may extend around an outer surface 152s of the structural material 152 of the outlet assembly 150, similarly to the second bayonet connector assembly 157 of FIGS. 2A-2B, and another bayonet connector sub-assembly that may be at least partially located within the interior of the outlet assembly 150 and may extend around an inner surface 152i of the structural material 152 to at least partially define a first portion 254 of the conduit 154 extending through the outlet assembly 150, similarly to the second bayonet connector assembly 157 of FIGS. 3A-3B.

Figure 4B:
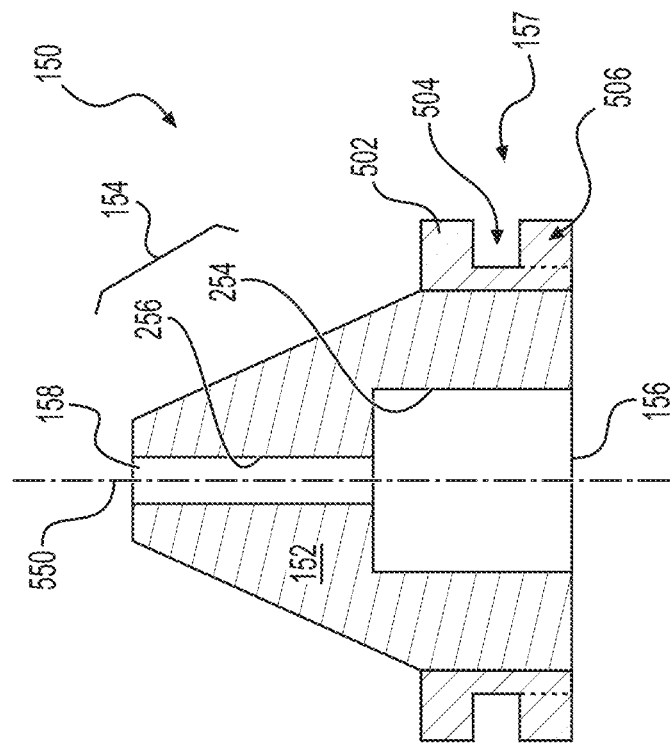
FIG. 4B is a cross-sectional view along line IVB-IVB' of the outlet assembly of FIG. 4A according to some example embodiments.
Figure 4A:
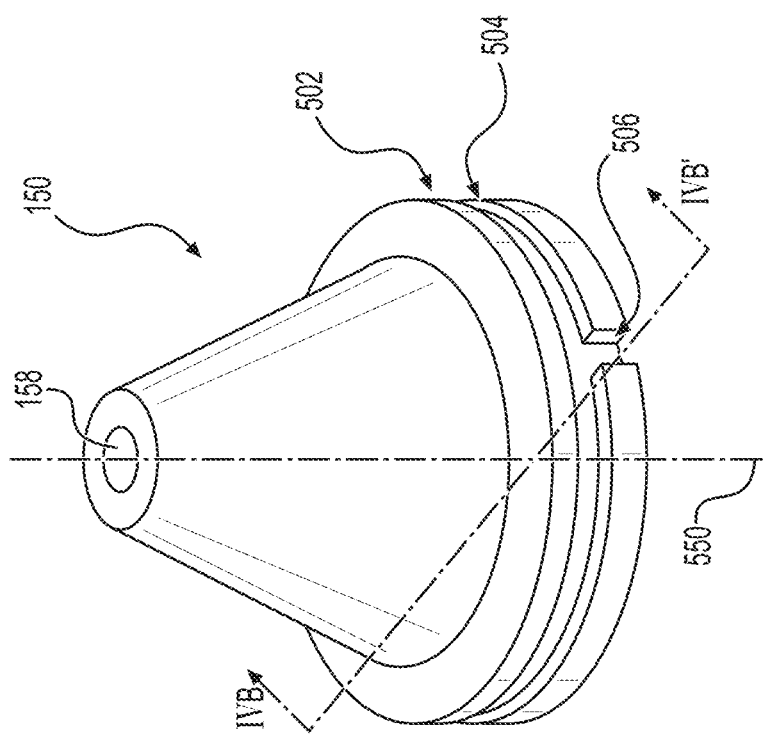
FIG. 4A is a perspective view of an outlet assembly according to some example embodiments.

FIG. 4A is a perspective view of an outlet assembly according to some example embodiments. FIG. 4B is a cross-sectional view along line IVB-IVB' of the outlet assembly of FIG. 4A according to some example embodiments. FIG. 4C is a perspective view of an outlet assembly according to some example embodiments. FIG. 4D is a cross-sectional view along line IVD-IVD' of the outlet assembly of FIG. 4C according to some example embodiments.

Referring to FIGS. 4A-4B, in some example embodiments, the second bayonet connector assembly 157 may include a radially outward-facing bayonet receptacle connector element that includes a base structure 502 with a circumferential groove 504 extending into the interior of the base structure 502 at least partially around the outer circumference of the base structure 502, and one or more coaxial channels 506 at least partially defined by base structure 502 that extend coaxially from an edge of the base structure 502 into the circumferential groove 504. In FIGS. 4A-4B, for example, the second bayonet connector assembly 157 includes two separate coaxial channels 506 extending along opposite outer sides of the output assembly 150. Referring to FIGS. 4C-4D, in some example embodiments, the first bayonet connector assembly 117 may include a radially inward facing bayonet plug connector element that includes a base structure 602 that extends around outer surface 119 to at least partially define partial enclosure 217 and one or more plug structures 604 that extend radially inward towards longitudinal axis 650 from the base structure 602. In FIGS. 4C-4D, for example, the first bayonet connector assembly 117 includes two separate plug structures 604 extending radially inward towards longitudinal axis 650 from opposite inner sides of the base structure 602.

Referring to FIGS. 4A-4D, the first bayonet connector assembly 117 as shown in FIGS. 4C-4D may be complementary to the second bayonet connector assembly 157 as shown in FIGS. 4A-4B, such that the bayonet receptacle connector element of the second bayonet connector assembly 157 is configured to engage with one or more plug structures 604 of the first bayonet connector assembly 117, based on at least the second bayonet connector assembly 157 being inserted into the partial enclosure 217, such that the one or more plug structures 604 are configured to be inserted into the circumferential groove 504 via the one or more coaxial channels 506, and the first and second bayonet connector assemblies 117, 157 are rotated around longitudinal axis 650 in relation to each other, to secure the one or more plug structures 604 within the circumferential groove 504 based on inducing mis-alignment of the one or more plug structures 604 with the one or more coaxial channels 506, thereby establishing the bayonet interface connection between the reservoir 112 and the outlet assembly 150.

FIG. 5A is a perspective view of an outlet assembly according to some example embodiments. FIG. 5B is a cross-sectional view along line VB-VB' of the outlet assembly of FIG. 5A according to some example embodiments. FIG. 5C is a perspective view of a reservoir assembly according to some example embodiments. FIG. 5D is a cross-sectional view along line VD-VD' of the reservoir assembly of FIG. 5C according to some example embodiments.

Referring to FIGS. 5A-5B, in some example embodiments, the second bayonet connector assembly 157 may include a radially outward facing bayonet plug connector element that includes one or more plug structures 512 that extend radially outward from a base structure 510 in relation to the longitudinal axis 550. As shown in FIGS. 5A-5B, for example, the second bayonet connector assembly 157 may include two plug structures 512 that extend radially outward from opposite outer sides of the base structure 510.

Referring to FIGS. 5C-5D, in some example embodiments, the first bayonet connector assembly 117 may include a radially inward-facing bayonet receptacle connector element that includes a base structure 602 extending around the outer surface 119 to at least partially define partial enclosure 217, a circumferential groove 612 extending into the interior of the base structure 602 to face radially inward to longitudinal axis 650 at least partially around the inner circumference of the base structure 602, and one or more coaxial channels 614 that extend coaxially in relation to longitudinal axis 650 into the circumferential groove 612 from an edge of the base structure 602. As shown in FIGS. 5C-5D, for example, the first bayonet connector assembly 117 may include two coaxial channels 614 extending along opposite inner sides of the base structure 602. Referring to FIGS. 5A-5D the first bayonet connector assembly 117 as shown in FIGS. 5C-5D may be complementary to the second bayonet connector assembly 157 as shown in FIGS. 5A-5B, such that the bayonet receptacle connector element of the first bayonet connector assembly 117 (e.g., circumferential groove 612 and coaxial channel(s) 614) is configured to engage with the bayonet plug connector element (e.g., plug structure(s) 512) of the second bayonet connector assembly 157, based on at least the second bayonet connector assembly 157 being inserted into the partial enclosure 217, such that the one or more plug structures 512 are configured to be inserted into the circumferential groove 612 via the one or more coaxial channels 614, and the first and second bayonet connector assemblies 117, 157 are rotated around longitudinal axis 650 in relation to each other, to secure the plug structure 512 within the circumferential groove 612 based on inducing mis-alignment of the one or more plug structures 512 with one or more coaxial channels 614, thereby establishing the bayonet interface connection between the reservoir 112 and the outlet assembly 150.

Figure 6A:
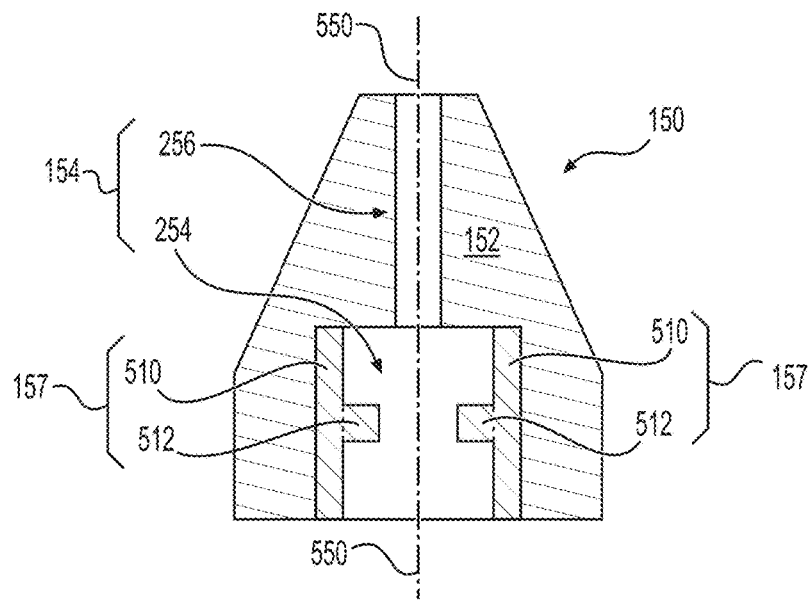
FIG. 6A is a cross-sectional view of an outlet assembly according to some example embodiments.
Figure 6B:
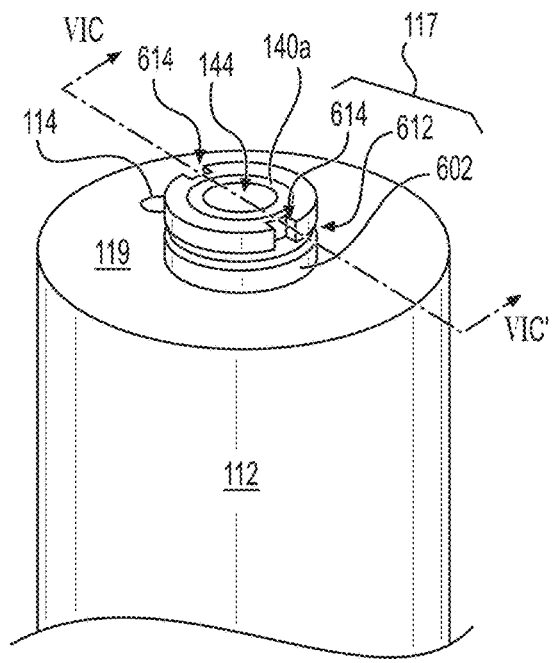
FIG. 6B is a perspective view of a reservoir assembly according to some example embodiments.
Figure 6C:
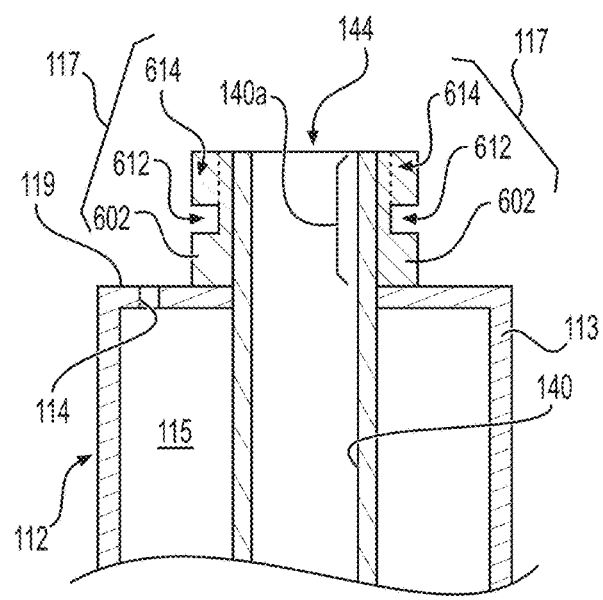
FIG. 6C is a cross-sectional view along line VIC-VIC' of the reservoir assembly of FIG. 6B according to some example embodiments.
Figure 7A:
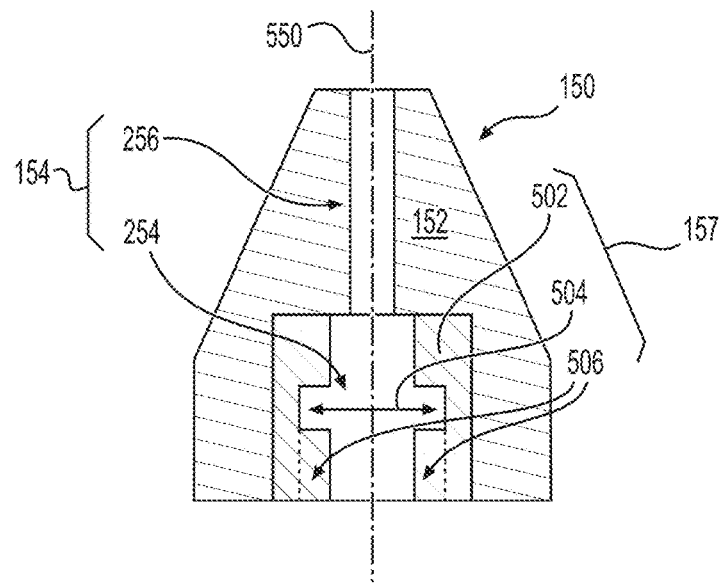
FIG. 7A is a cross-sectional view of an outlet assembly according to some example embodiments.
Figure 7B:
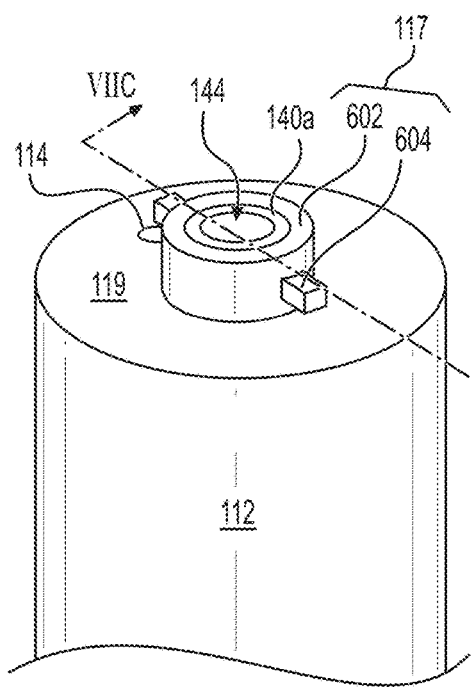
FIG. 7B is a perspective view of a reservoir assembly according to some example embodiments.
Figure 7C:
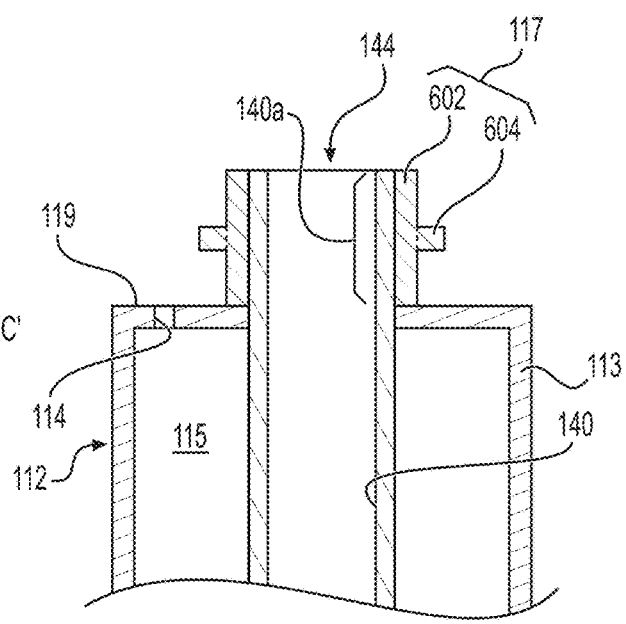
FIG. 7C is a cross-sectional view along line VIIC-VIIC' of the reservoir assembly of FIG. 7B according to some example embodiments.

FIG. 6A is a cross-sectional view of an outlet assembly according to some example embodiments. FIG. 6B is a perspective view of a reservoir assembly according to some example embodiments. FIG. 6C is a cross-sectional view along line VIC-VIC' of the reservoir assembly of FIG. 6B according to some example embodiments. FIG. 7A is a cross-sectional view of an outlet assembly according to some example embodiments. FIG. 7B is a perspective view of a reservoir assembly according to some example embodiments. FIG. 7C is a cross-sectional view along line VIIC-VIIC' of the reservoir assembly of FIG. 7B according to some example embodiments.

Referring to FIGS. 6A and 7A, in some example embodiments, the second bayonet connector assembly 157 may include a bayonet plug connector element (e.g., plug structure(s) 512 as shown in FIG. 6A) or a bayonet receptacle connector element (e.g., circumferential groove 504 and coaxial channel(s) 506 as shown in FIG. 7A) within an interior of the outlet assembly 150 and at least partially defining a first portion 254 of a conduit 154 extending through the interior of the outlet assembly 150 and which is configured to receive at least a first end 140a of conduit 140 therein when the outlet assembly 150 is detachably coupled with reservoir 112. Referring now to FIGS. 6B-6C and FIGS. 7B-7C, in some example embodiments, the first bayonet connector assembly 117 may extend around the first end 140a of the conduit 140 and include a radially-outward facing bayonet receptacle connector element (e.g., circumferential groove 612 and coaxial channel(s) 614 as shown in FIGS. 6B-6C) or a radially outward facing bayonet plug connector element (e.g., plug structure(s) 604 as shown in FIGS. 7B-7C). The second bayonet connector assembly 157 shown in FIG. 6A may be complementary with the first bayonet connector assembly 117 shown in FIGS. 6B-6C, and the second bayonet connector assembly 157 shown in FIG. 7A may be complementary with the first bayonet connector assembly 117 shown in FIGS. 7B-7C.

Figure 8D:
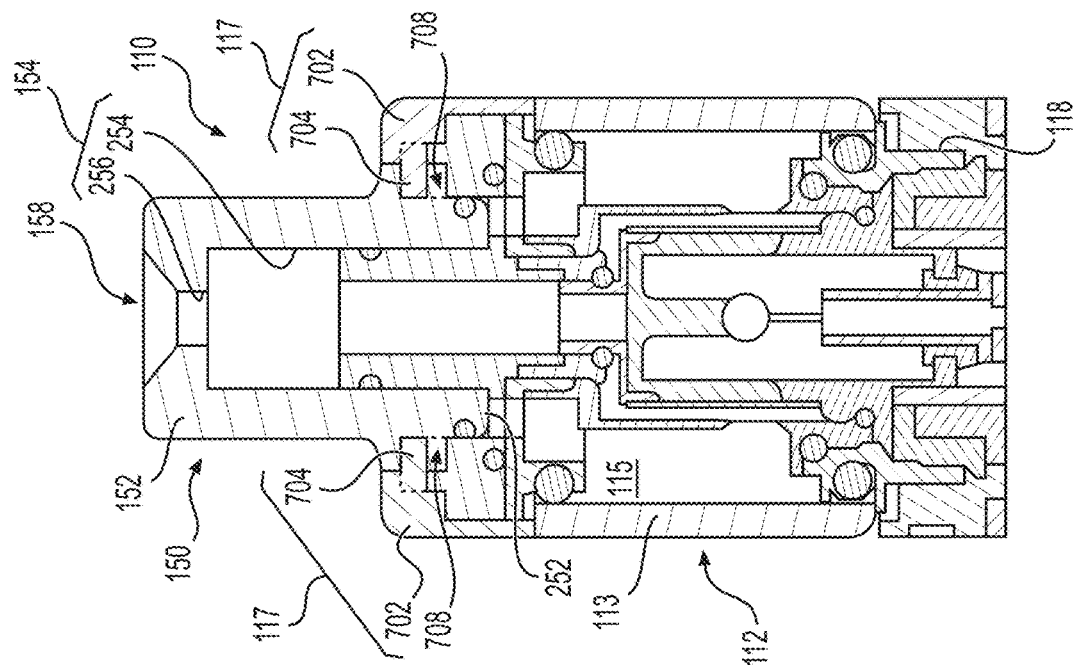
FIG. 8D is a cross-sectional view along line VIIID-VIIID' of the coupled reservoir and outlet assembly of FIG. 8C according to some example embodiments.
Figure 8C:
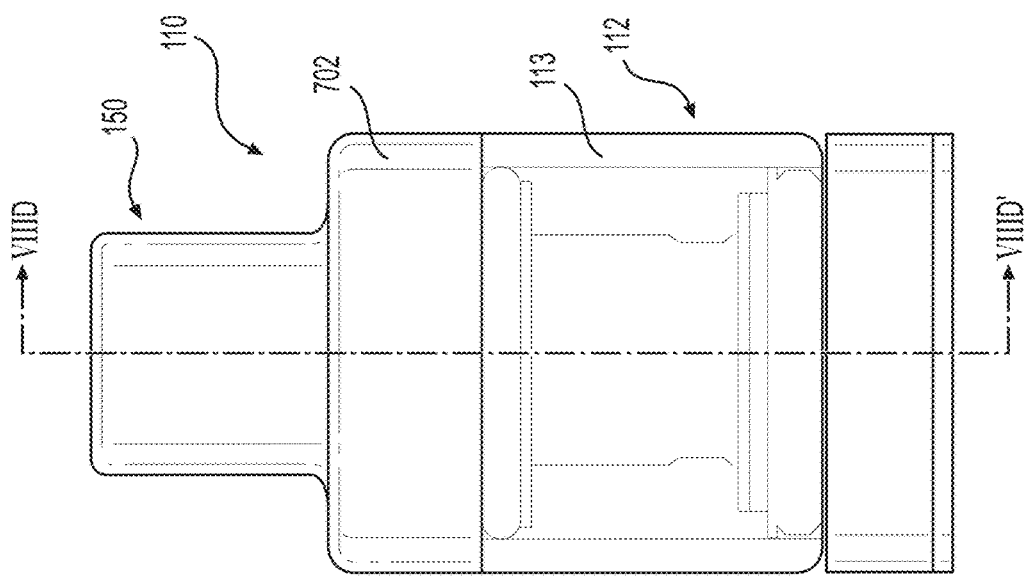
FIG. 8C is a side view of a reservoir and an outlet assembly coupled with the reservoir according to some example embodiments.

FIG. 8A is a side view of a reservoir and an outlet assembly decoupled from the reservoir according to some example embodiments. FIG. 8B is a cross-sectional view along line VIIIB-VIIIB' of the decoupled reservoir and outlet assembly of FIG. 8A according to some example embodiments. FIG. 8C is a side view of a reservoir and an outlet assembly coupled with the reservoir according to some example embodiments. FIG. 8D is a cross-sectional view along line VIIID-VIIID' of the coupled reservoir and outlet assembly of FIG. 8C according to some example embodiments. FIG. 8E is a perspective view of the decoupled reservoir and outlet assembly of FIG. 8A according to some example embodiments. FIG. 8F is a perspective view of the decoupled reservoir and outlet assembly of FIG. 8E according to some example embodiments. FIG. 8G is a perspective view of a reservoir and an outlet assembly coupled with the reservoir according to some example embodiments. FIG. 9A is a perspective view of an outlet assembly according to some example embodiments. FIG. 9B is a cross-sectional view along line IXB-IXB' of the outlet assembly of FIG. 9A according to some example embodiments. FIG. 9C is a perspective view of a bayonet connector assembly according to some example embodiments.

As shown in FIGS. 8A-9C, in some example embodiments, the first and second bayonet connector assemblies 117, 157 may be similar to the first and second bayonet connector assemblies 117, 157 shown in FIGS. 4A-4D, where the first bayonet connector assembly 117 may include a radially inward facing bayonet plug connector element that includes two plug structures 704 extending radially inward from opposite inner sides of a base structure 702 that extends around a longitudinal axis of the vapor generator assembly 110, and the second bayonet connector assembly 157 may include a radially outward facing bayonet receptacle connector element that includes circumferential groove 706 and two coaxial channels 708 extending along opposite outer sides of the second bayonet connector assembly 157. As shown in FIGS. 8A-9C, the outlet assembly 150 may include an instance of structural material 152 that defines a cylindrical outer surface of at least a portion of the outlet assembly, and at least a portion of the housing 111 of the vapor generator assembly 110 (e.g., at least a portion of the housing 113 of the reservoir 112) may be transparent or translucent to visible light.

As shown in at least FIGS. 8E-8G, detachably coupling the first and second bayonet connector assemblies 117, 157 of the reservoir 112 and outlet assembly 150, respectively, may include inserting 790 at least the second bayonet connector assembly 157 into the partial enclosure 217, such that coaxial channel(s) 708 of the second bayonet connector assembly 157 is (or are) aligned with the plug structure(s) 704 of the first bayonet connector assembly 117 and the inserting 790 results in the plug structure(s) 704 being received into circumferential groove 706 via the coaxial channel(s) 708.

As shown in FIGS. 8A-9C, in some example embodiments the first bayonet connector assembly 117 includes at least two plug structures 704 extending radially inward from opposite inner sides of a base structure 702, and the second bayonet connector assembly 157 includes at least two coaxial channels 708 extending along opposite outer sides of the second bayonet connector assembly to the circumferential groove 706, but example embodiments are not limited thereto. For example, in some embodiments, the first bayonet connector assembly 117 may include only one plug structure 704, and/or the second bayonet connector assembly 157 may include only one coaxial channel 708. In another example, the first bayonet connector assembly 117 may include two or more plug structures 704, and/or the second bayonet connector assembly 157 may include two or more coaxial channels 708. The detachably coupling of the first and second bayonet connector assemblies 117, 157 may further include rotating 792 the outlet assembly 150 in relation to the reservoir 112 around the longitudinal axis of the vapor generator assembly 110, so that the plug structure(s) 704 of the first bayonet connector assembly 117 moves (or move) through circumferential groove 706 to become mis-aligned with the coaxial channel(s) 708 to complete the bayonet interface connection between the reservoir 112 and the outlet assembly 150.

As shown in FIGS. 8A-9C, the first bayonet connector assembly 117 may include a base structure 702 that forms an upper lip structure that extends around a top edge of the inner side(s) of the base structure 702, and the plug structure(s) 704) may extend from the inner side(s) of the base structure 702 and beyond the edge(s) of the upper lip structure. As further shown in FIGS. 8A-8G, the plug structure(s) 704 may extend through a separate structure that is located within the space(s) bounded by the inner side(s) of the base structure 702 and the upper lip structure of the base structure 702.

Detaching the outlet assembly 150 from the reservoir 112 may include performing the reverse of the above process, where the outlet assembly 150 is rotated 792 in relation to the reservoir 112 to cause the plug structure(s) 704 to move through circumferential groove 706 to be aligned with the coaxial channel(s) 708 and then removing the outlet assembly 150 from the partial enclosure 217 such that the plug structure 704 moves through the aligned coaxial channel 708 to disengage from the second bayonet connector assembly 157 via the coaxial channel 708.

It will be understood that the rotation 792 shown in FIG. 8G is not limited to the direction shown in FIG. 8G. For example, the rotation 792 could be clockwise and/or counter-clockwise. In some example embodiments, the rotation 792 to detachably couple the outlet assembly 150 to the reservoir 112 is in the same direction as the rotation 792 to detach the outlet assembly 150 from the reservoir 112. In some example embodiments, the rotation 792 to detachably couple the outlet assembly 150 to the reservoir 112 is in an opposite direction as the rotation 792 to detach the outlet assembly 150 from the reservoir 112.

The first bayonet connector assembly 117 and/or the second bayonet connector assembly 157 may be configured to generate an audible signal (e.g., a "click" sound) based on interaction between elements of the first and second bayonet connector assemblies 117, 157 as a result of the bayonet interface connection between the reservoir 112 and the outlet assembly 150 being established or terminated via coupling or decoupling of the first and second bayonet connector assemblies 117, 157, respectively. In some example embodiments, the first bayonet connector assembly 117 and/or the second bayonet connector assembly 157 may include a structure that is configured to arrest rotation 792 to detachably couple the outlet assembly 150 the reservoir 112, in order to prevent re-alignment of the coaxial channel(s) 708 of the second bayonet connector assembly 157 with the plug structure(s) 704 of the first bayonet connector assembly 117, thereby preventing inadvertent detachment of the outlet assembly 150 from the reservoir 112 when attempting to detachably couple the outlet assembly 150 to the reservoir 112. In some example embodiments, such a structure may be absent from both the first and second bayonet connector assemblies 117, 157, such that the rotation 792 of the rotation of the outlet assembly 150 when the plug structure(s) 704 are received into the circumferential groove 706 is unrestricted.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A reservoir assembly for an e-vaping device, the reservoir assembly comprising:
   a reservoir configured to hold pre-vapor formulation;
   a first bayonet connector assembly at a first end of the reservoir, the first bayonet connector assembly including a base structure extending around an outer surface of an outer housing of the reservoir, such that the outer housing and the base structure at least partially define a partial enclosure; and
   a conduit having a first end extending through the outer housing of the reservoir, out of the reservoir, and into the partial enclosure,
   wherein the first bayonet connector assembly is configured to detachably couple with a second bayonet connector assembly of an outlet assembly to establish a bayonet interface connection between the reservoir and the outlet assembly, the outlet assembly having one or more inner surfaces that define an outlet assembly conduit extending through an interior of the outlet assembly between opposite, first and second openings, the outlet assembly conduit including a first conduit portion and a second conduit portion, the first conduit portion being proximate to the first opening of the outlet assembly and having a first diameter and a first length that are at least equal to a corresponding diameter and length, respectively of the first end of the conduit such that when the bayonet interface connection is established,
      a portion of the outlet assembly is located within the partial enclosure between the first end of the conduit and the base structure of the first bayonet connector assembly and contacts the outer surface of the outer housing of the reservoir,
      the first end of the conduit is inserted into and enclosed within the first conduit portion of the outlet assembly conduit via the first opening of the outlet assembly, and
      the conduit is in fluid communication with an exterior of the reservoir assembly through the first end of the conduit and the outlet assembly conduit,
   wherein the reservoir includes a fluid port that is separate from the conduit and extends through the outer housing of the reservoir to the outer surface of the outer housing at the first end of the reservoir, the fluid port configured to enable refilling of pre-vapor formulation in the reservoir via the fluid port,
   wherein the first bayonet connector assembly is configured to cause the fluid port to be isolated from the exterior of the reservoir assembly by the outlet assembly based on the bayonet interface connection being established, such that
      the fluid port is between the outlet assembly and the reservoir, and
      the reservoir is isolated, by at least the outlet assembly, from fluid communication with the exterior of the reservoir assembly through the fluid port based on the portion of the outlet assembly being in the partial enclosure and contacting the outer surface of the outer housing of the reservoir.

2. The reservoir assembly of claim 1, wherein
   the conduit extends from a vaporizer assembly at a second end of the reservoir, wherein the first and second ends of the reservoir are opposite ends of the reservoir such that the first bayonet connector assembly and the vaporizer assembly are at opposite ends of the reservoir,
   the vaporizer assembly is in fluid communication with the exterior of the reservoir assembly through the interior of the outlet assembly when the bayonet interface connection is established,
   the fluid port is configured to enable refilling of pre-vapor formulation in the reservoir via the fluid port and independently of the vaporizer assembly, and
   the first bayonet connector assembly is configured to cause the fluid port to be isolated from the exterior of the reservoir assembly by the outlet assembly based on the bayonet interface connection being established, such that
      the reservoir is isolated, by at least the outlet assembly, from fluid communication with the exterior of the reservoir assembly independently of the vaporizer assembly.

3. The reservoir assembly of claim 1, wherein the conduit extends through the partial enclosure.

4. The reservoir assembly of claim 1, wherein the first bayonet connector assembly includes a bayonet plug connector element and is configured to detachably couple with a complementary bayonet receptacle connector element of the second bayonet connector assembly to establish the bayonet interface connection.

5. The reservoir assembly of claim 2, further comprising:
   a vaporizer connector assembly configured to detachably couple the reservoir with the vaporizer assembly.

6. The reservoir assembly of claim 5, wherein an end of the conduit is coupled to the vaporizer connector assembly, such that the conduit is configured to couple with the vaporizer assembly via the vaporizer connector assembly.

7. The reservoir assembly of claim 1, wherein the first bayonet connector assembly is directly coupled to the first end of the reservoir.

8. A vapor generator assembly for an e-vaping device, the vapor generator assembly comprising:
   a reservoir and a vaporizer assembly, the reservoir configured to supply pre vapor formulation to the vaporizer assembly;
   a first bayonet connector assembly at a first end of the reservoir, wherein the vaporizer assembly is at a second end of the reservoir, and the first and second ends of the reservoir are opposite ends of the reservoir such that the first bayonet connector assembly and the vaporizer assembly are at opposite ends of the reservoir, the first bayonet connector assembly including a base structure extending around an outer surface of an outer housing of the reservoir such that the outer housing and the base structure at least partially define a partial enclosure; and
   a conduit having a first end extending from the vaporizer assembly, through the outer housing of the reservoir, out of the reservoir, and into the partial enclosure, the conduit configured to enable fluid communication between the vaporizer assembly and an exterior of the vapor generator assembly through the first bayonet connector assembly; and an outlet assembly including a second bayonet connector assembly, the second bayonet connector assembly detachably coupled to the first bayonet connector assembly to establish a bayonet interface connection between the reservoir and the outlet assembly, the outlet assembly having one or more inner surfaces that define an outlet assembly conduit extending through an interior of the outlet assembly between opposite, first and second openings, the outlet assembly conduit including a first conduit portion and a second conduit portion, the first conduit portion being proximate to the first opening of the outlet assembly and having a first diameter and a first length that are at least equal to a corresponding diameter and length, respectively of the first end of the conduit such that when the bayonet interface connection is established,
- a portion of the outlet assembly is located within the partial enclosure between the first end of the conduit and the base structure of the first bayonet connector assembly and contacts the outer surface of the outer housing of the reservoir,
- the first end of the conduit is inserted into and enclosed within the first conduit portion of the outlet assembly conduit via the first opening of the outlet assembly,
- the conduit is in fluid communication with the exterior of the vapor generator assembly through the first end of the conduit and the outlet assembly conduit, and
- the vaporizer assembly is in fluid communication with the exterior of the vapor generator assembly through the conduit and the outlet assembly conduit, wherein the reservoir includes a fluid port that is separate from the conduit and extends through the outer housing of the reservoir to the outer surface of the outer housing at the first end of the reservoir, the fluid port configured to enable refilling of pre-vapor formulation in the reservoir via the fluid port independently of the vaporizer assembly, wherein the outlet assembly is configured to isolate the fluid port from the exterior of the vapor generator assembly based on the bayonet interface connection being established, such that
- the fluid port is between the outlet assembly and the reservoir, and
- the reservoir is isolated, by at least the outlet assembly, from fluid communication with the exterior of the vapor generator assembly independently of the vaporizer assembly based on the portion of the outlet assembly being in the partial enclosure and contacting the outer surface of the outer housing of the reservoir.

9. The vapor generator assembly of claim 8, wherein the conduit extends through the partial enclosure.

10. The vapor generator assembly of claim 8, wherein the first bayonet connector assembly includes a bayonet plug connector and is configured to detachably couple with a bayonet receptacle connector of the second bayonet connector assembly to establish the bayonet interface connection.

11. The vapor generator assembly of claim 8, further comprising:
a vaporizer connector assembly, wherein the reservoir is detachably coupled with the vaporizer assembly through the vaporizer connector assembly.

12. The vapor generator assembly of claim 11, wherein an end of the conduit is coupled to the vaporizer connector assembly, such that the conduit is coupled with the vaporizer assembly via the vaporizer connector assembly.

13. The vapor generator assembly of claim 8, wherein the first bayonet connector assembly is directly coupled to the first end of the reservoir.

14. An e-vaping device, comprising:
the vapor generator assembly according to claim 8; and
a power supply assembly coupled to the vapor generator assembly, the power supply assembly including a power supply, the power supply assembly configured to supply electrical power from the power supply to the vaporizer assembly of the vapor generator assembly.

15. The e-vaping device of claim 14, wherein the conduit extends through the partial enclosure.

16. The e-vaping device of claim 14, wherein the first bayonet connector assembly includes a bayonet plug connector and is configured to detachably couple with a bayonet receptacle connector of the second bayonet connector assembly to establish the bayonet interface connection.

17. The e-vaping device of claim 14, wherein the first bayonet connector assembly is directly coupled to the first end of the reservoir.

18. The e-vaping device of claim 14, wherein the power supply assembly includes a rechargeable battery.

19. The e-vaping device of claim 14, wherein the power supply assembly is detachably coupled with the vapor generator assembly.

20. The e-vaping device of claim 14, further comprising:
a vaporizer connector assembly, wherein the reservoir is detachably coupled with the vaporizer assembly through the vaporizer connector assembly.

* * * * *